(12) United States Patent
Nishiyama

(10) Patent No.: US 10,570,197 B2
(45) Date of Patent: Feb. 25, 2020

(54) FD CHAIN GENE OR L CHAIN GENE CAPABLE OF INCREASING SECRETION AMOUNT OF FAB-TYPE ANTIBODY

(71) Applicant: KANEKA CORPORATION, Osaka-shi, Osaka (JP)

(72) Inventor: Tozo Nishiyama, Takasago (JP)

(73) Assignee: KANEKA CORPORATION, Osaka-Shi (JP)

( * ) Notice: Subject to any disclaimer, the term of this patent is extended or adjusted under 35 U.S.C. 154(b) by 58 days.

(21) Appl. No.: 14/921,497

(22) Filed: Oct. 23, 2015

(65) Prior Publication Data

US 2016/0122428 A1    May 5, 2016

Related U.S. Application Data

(63) Continuation-in-part of application No. PCT/JP2014/060941, filed on Apr. 17, 2014.

(30) Foreign Application Priority Data

Apr. 25, 2013   (JP) .................. 2013-092862
Oct. 25, 2013   (JP) .................. 2013-221703

(51) Int. Cl.
| | | |
|---|---|---|
| C12N 15/81 | (2006.01) | |
| C12N 15/09 | (2006.01) | |
| C12N 1/19 | (2006.01) | |
| C07K 16/00 | (2006.01) | |
| C12P 21/08 | (2006.01) | |
| C07K 16/24 | (2006.01) | |

(52) U.S. Cl.
CPC .......... C07K 16/241 (2013.01); C12N 15/815 (2013.01); *C07K 2317/55* (2013.01); *C07K 2317/76* (2013.01)

(58) Field of Classification Search
CPC .. C07K 16/241; C07K 16/00; C07K 2319/01; C07K 2317/14; C07K 2317/55; C12N 15/815; C12N 15/81; C12N 15/63; C12N 1/19; C12P 21/02; A61K 47/6845
See application file for complete search history.

(56) References Cited

FOREIGN PATENT DOCUMENTS

| | | |
|---|---|---|
| EP | 2 489 724 A1 | 8/2012 |
| EP | 2 669 375 A1 | 12/2013 |
| JP | 63-503274 A | 12/1988 |
| JP | 3-501321 A | 3/1991 |
| JP | 3-280884 A | 12/1991 |
| JP | 7-503124 A | 4/1995 |
| JP | 2006-320220 A | 11/2006 |
| JP | 2007-215471 A | 8/2007 |
| JP | 2009-508486 A | 3/2009 |
| JP | 2009-82033 A | 4/2009 |
| JP | 2013-55935 A | 3/2013 |
| WO | WO 89/00999 A1 | 2/1989 |
| WO | WO 92/22324 A1 | 12/1992 |
| WO | WO 2007/035283 A1 | 3/2007 |
| WO | WO 2010/124018 A1 | 10/2010 |
| WO | WO 2012/102171 A1 | 8/2012 |

OTHER PUBLICATIONS

Lange et al., J Immunological Methods 255: 103-114; 2001.*
Takai et al., J Biochem 129: 5-12; 2001.*
Takahashi et al., Biosci Biotechnol Biochem 64: 2138-2144, 2000.*
Rudikoff et al., Proc Natl Acad Sci USA vol. 79 pp. 1979-1983, 1982.*
Jubala et al., Vet Pathol 42: 468-476, 2005.*
Edwards et al., J Mol Biol 334(1): 103-118 (Year: 2003).*
Lloyd et al., Protein Engineering, Design & Selection 22: 159-168 (Year: 2009).*
Horwitz et al., Proc Natl Acad Sci USA 85: 8678-8682 (Year: 1988).*
Abdel-Salam, H.A., et al, "Expression of Heavy Chain Peptide Gamma of Mouse Anticreatine Kinase IgG Antibody in the Yeast *Hansenula polymorpha*," The Chinese Pharmaceutical Journal, Jan. 1, 2004, vol. 56, pp. 147-158.
Abdel-Salam, H.A., et al, "Expression of mouse anticreatine kinase (MAK33) monoclonal antibody in the yeast *Hansenula polymorpha*," Appl Microbiol Biotechnol, Jan. 1, 2001, vol. 56, pp. 157-164.
Extended European Search Report for Appl. No. 14788127.0 dated Dec. 12, 2016.
Song, H., et al, "Development of a set of expression vectors in Hansenula Polymorpha," Biotechnology Letters, Jan. 1, 2003, vol. 25, pp. 1999-2006.
Bolognesi et al., "A Comparison of Anti-Lymphocyte Immunotoxins Containing Different Ribosome-Inactivating Proteins and Antibodies," Clin. Exp. Immunol., 1992, vol. 89, pp. 341-346.
Casellas et al., "Trichokirin, a Ribosome-Inactivating Protein from the Seeds of Trichosanthes kirilowii Maximowicz," Eur. J. Biochem., 1988, vol. 176, pp. 581-588.
Chen et al., "Selection and Analysis of an Optimized Anti-VEGF Antibody: Crystal Structure of an Affinity-matured Fab in Complex with Antigen," J. Mol. Biol., 1999, vol. 293, pp. 865-881.
Cumber et al., "Purification of Immunotoxins Containing the Ribosome-Inactivating Proteins Gelonin and Momordin Using High Performance Liquid Immunoaffinity Chromatography Compared with Blue Sepharose CL-6B Affinity Chromatography," J. Immunol. Methods, vol. 135, 1990, pp. 15-24.

(Continued)

Primary Examiner — Phuong Huynh
(74) Attorney, Agent, or Firm — Birch, Stewart, Kolasch & Birch, LLP

(57) ABSTRACT

It is an object of the present invention to provide a method for producing a low-molecular-weight antibody such as a Fab-type antibody, using yeast as a host, wherein the method is able to produce the low-molecular-weight antibody with high productivity. According to the present invention, there is provided a gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain or L chain of an antibody.

7 Claims, No Drawings
Specification includes a Sequence Listing.

(56) References Cited

OTHER PUBLICATIONS

EMEA, "Refusal Asessment Report for Cimzia," London, Mar. 19, 2008, EMEA/176303/2008, pp. 1-50.

Fulton et al., "Purification of Ricin $A_1$, $A_2$, and B Chains and Characterization of Their Toxicity," The Journal of Biological Chemistry, vol. 261, No. 12, Apr. 25, 1986, pp. 5314-5319.

Gasser et al., "Engineering of Pichia pastoris for Improved Production of Antibody Fragments," Biotechnology and Bioengineering, vol. 94, No. 2, Jun. 5, 2006 (published online Mar. 28, 2006), pp. 353-361.

Ghetie et al., "The GLP Large Scale Preparation of Immunotoxins Containing Deglycosylated Ricin A Chain and a Hindered Disulfide Bond," Journal of Immunological Methods, vol. 142, 1991, pp. 223-230.

International Preliminary Report on Patentability and Written Opinion of the International Searching Authority (Forms PCT/IB/338, PCT/IB/373, PCT/IB/326 and PCT/ISA/237), dated Nov. 5, 2015, for International Application No. PCT/JP2014/060941, with an English translation of the Written Opinion.

International Search Report (Forms PCT/ISA/220 and PCT/ISA/210), dated Jul. 15, 2014, for International Application No. PCT/JP2014/060941.

Oeltmann et al., "[29] Preparation of Diphtheria Toxin Fragment A Coupled to Hormone," Methods in Enzymology, vol. 165, 1988, pp. 204-210.

Pai et al., "Treatment of Advanced Solid Tumors with Immunotoxin LMB-1: An Antibody Linked to Pseudomonas Exotoxin," Nature Medicine, vol. 2, No. 3, Mar. 1996, pp. 350-353.

Sivam et al., "Immunotoxins to a Human Melanoma-associated Antigen: Comparison of Gelonin with Ricin and Other A Chain Conjugates," Cancer Research, vol. 47, Jun. 15, 1987, pp. 3169-3173 (6 pages).

Stirpe et al., "Ribosome-inactivating Proteins up to Date," FEBS Letters, vol. 195, No. 1-2, Jan. 1986, pp. 1-8.

Thorpe et al., "New Coupling Agents for the Synthesis of Immunotoxins Containing a Hindered Disulfide Bond with Improved Stability in Vivo," Cancer Research, vol. 47, Nov. 15, 1987, pp. 5924-5931 (9 pages).

Wawrzynczak et al., "Molecular and Biological Properties of an Abrin A Chain Immunotoxin Designed for Therapy of Human Small Cell Lung Cancer," Br. J. Cancer, 1992, vol. 66, pp. 361-366.

Wawrzynczak et al., "Pharmacokinetics in the Rat of a Panel of Immunotoxins Made with Abrin A Chain, Ricin A Chain, Gelonin, and Momordin," Cancer Research, vol. 50, Dec. 1, 1990, pp. 7519-7526 (9 pages).

Japanese Office Action, dated Jan. 9, 2018, for Japanese Application No. 2015-513720, as well as an English machine translation.

Japanese Office Action with the English translation issued in Japanese Application No. 2015-513720 dated Aug. 28, 2018.

Office Action issued in Indian Patent Application No. 3846/KOLNP/2015 dated Dec. 30, 2019.

\* cited by examiner

SEQUENCE LISTING

<160> NUMBER OF SEQ ID NOS: 78

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Asp Lys Thr His
1

<210> SEQ ID NO 2

```
<211> LENGTH: 5
<212> TYPE: PRT
<213> ORGANISM: Artificial Sequence
<220> FEATURE:
<223> OTHER INFORMATION: Synthetic

<400> SEQUENCE: 2

Asp Lys Thr His Thr
1               5

<210> SEQ ID NO 3
<211> LENGTH: 12
<212> TYPE: DNA
<213> ORGANISM: Artificial Sequence
<220> FEATURE:
<223> OTHER INFORMATION: Synthetic

<400> SEQUENCE: 3
gacaagaccc ac                                                         12

<210> SEQ ID NO 4
<211> LENGTH: 15
<212> TYPE: DNA
<213> ORGANISM: Artificial Sequence
<220> FEATURE:
<223> OTHER INFORMATION: Synthetic

<400> SEQUENCE: 4
gacaagaccc acacc                                                      15

<210> SEQ ID NO 5
<211> LENGTH: 678
<212> TYPE: DNA
<213> ORGANISM: Homo sapiens

<400> SEQUENCE: 5
gaggtgcagc tggtggagtc tggggggaggc ttggtacagc ccggcaggtc cctgagactc    60
tcctgtgcgg cctctggatt cacctttgat gattatgcca tgcactgggt ccggcaagct   120
ccagggaagg gcctggaatg ggtctcagct atcacttgga atagtggtca catagactat   180
gcggactctg tgagggccg attcaccatc tccagagaca cgccaagaa ctccctgtat    240
ctgcaaatga acagtctgag agctgaggat acggccgtat attactgtgc gaaagtctcg   300
taccttagca ccgcgtcctc ccttgactat tggggccaag gaccctggt caccgtctcg    360
agtgctagct tcaagggccc atcggtcttc cccctggcac cctcctccaa gagcacctct   420
gggggcacag cggccctggg ctgcctggtc aaggactact cccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgactaa                                                  678

<210> SEQ ID NO 6
<211> LENGTH: 681
<212> TYPE: DNA
<213> ORGANISM: Homo sapiens

<400> SEQUENCE: 6
gaggtgcagc tggtggagtc tggggggaggc ttggtacagc ccggcaggtc cctgagactc    60
tcctgtgcgg cctctggatt cacctttgat gattatgcca tgcactgggt ccggcaagct   120
```

```
ccagggaagg gcctggaatg ggtctcagct atcacttgga atagtggtca catagactat      180
gcggactctg tggagggccg attcaccatc tccagagaca acgccaagaa ctccctgtat      240
ctgcaaatga acagtctgag agctgaggat acggccgtat attactgtgc gaaagtctcg      300
taccttagca ccgcgtcctc ccttgactat tggggccaag ggaccctggt caccgtctcg      360
agtgctagct tcaagggccc atcggtcttc cccctggcac cctcctccaa gagcacctct      420
gggggcacag cggccctggg ctgcctggtc aaggactact tccccgaacc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gagagttgag      660
cccaaatctt gtgacaagta a                                               681

<210> SEQ ID NO 7
<211> LENGTH: 684
<212> TYPE: DNA
<213> ORGANISM: Homo sapiens

<400> SEQUENCE: 7
gaggtgcagc tggtggagtc tgggggaggc ttggtacagc ccggcaggtc cctgagactc       60
tcctgtgcgg cctctggatt cacctttgat gattatgcca tgcactgggt ccggcaagct      120
ccagggaagg gcctggaatg ggtctcagct atcacttgga atagtggtca catagactat      180
gcggactctg tggagggccg attcaccatc tccagagaca acgccaagaa ctccctgtat      240
ctgcaaatga acagtctgag agctgaggat acggccgtat attactgtgc gaaagtctcg      300
taccttagca ccgcgtcctc ccttgactat tggggccaag ggaccctggt caccgtctcg      360
agtgctagct tcaagggccc atcggtcttc cccctggcac cctcctccaa gagcacctct      420
gggggcacag cggccctggg ctgcctggtc aaggactact tccccgaacc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gagagttgag      660
cccaaatctt gtgacaagac ctaa                                            684

<210> SEQ ID NO 8
<211> LENGTH: 687
<212> TYPE: DNA
<213> ORGANISM: Homo sapiens

<400> SEQUENCE: 8
gaggtgcagc tggtggagtc tgggggaggc ttggtacagc ccggcaggtc cctgagactc       60
tcctgtgcgg cctctggatt cacctttgat gattatgcca tgcactgggt ccggcaagct      120
ccagggaagg gcctggaatg ggtctcagct atcacttgga atagtggtca catagactat      180
gcggactctg tggagggccg attcaccatc tccagagaca acgccaagaa ctccctgtat      240
ctgcaaatga acagtctgag agctgaggat acggccgtat attactgtgc gaaagtctcg      300
taccttagca ccgcgtcctc ccttgactat tggggccaag ggaccctggt caccgtctcg      360
agtgctagct tcaagggccc atcggtcttc cccctggcac cctcctccaa gagcacctct      420
gggggcacag cggccctggg ctgcctggtc aaggactact tccccgaacc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
```

```
acctacatct gcaacgtgaa tcacaagccc agcaacacca aggtggacaa gagagttgag    660
cccaaatctt gtgacaagac ccactaa                                        687

<210> SEQ ID NO 9
<211> LENGTH: 690
<212> TYPE: DNA
<213> ORGANISM: Homo sapiens

<400> SEQUENCE: 9
gaggtgcagc tggtggagtc tggggggaggc ttggtacagc ccggcaggtc cctgagactc    60
tcctgtgcgg cctctggatt cacctttgat gattatgcca tgcactgggt ccggcaagct   120
ccagggaagg gcctggaatg ggtctcagct atcacttgga atagtggtca catagactat   180
gcggactctg tggagggccg attcaccatc tccagagaca cgccaagaa ctccctgtat    240 ctgcaaatga acagtctgag agctgaggat acggccgtat attactgtgc gaaagtctcg   300
taccttagca ccgcgtcctc ccttgactat tggggccaag ggaccctggt caccgtctcg   360
agtgctagct tcaagggccc atcggtcttc cccctggcac cctcctccaa gagcacctct   420
gggggcacag cggccctggg ctgcctggtc aaggactact ccccgaacc ggtgacggtg    480 tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaagac ccacacctaa                                    690

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
ataaagatct gaggtgcagc tggtggagtc                                      30

<210> SEQ ID NO 11
<211> LENGTH: 39
<212> TYPE: DNA
<213> ORGANISM: Artificial Sequence
<220> FEATURE:
<223> OTHER INFORMATION: Synthetic

<400> SEQUENCE: 11
tataagatct ttagtcacaa gatttgggct caactctct                            39

<210> SEQ ID NO 12
<211> LENGTH: 42
<212> TYPE: DNA
<213> ORGANISM: Artificial Sequence
<220> FEATURE:
<223> OTHER INFORMATION: Synthetic

<400> SEQUENCE: 12
tataagatct ttacttgtca caagatttgg gctcaactct ct                        42

<210> SEQ ID NO 13
<211> LENGTH: 45
<212> TYPE: DNA
<213> ORGANISM: Artificial Sequence
<220> FEATURE:
```

<223> OTHER INFORMATION: Synthetic

<400> SEQUENCE: 13
tataagatct ttaggtcttg tcacaagatt tgggctcaac tctct      45

<210> SEQ ID NO 14
<211> LENGTH: 45
<212> TYPE: DNA
<213> ORGANISM: Artificial Sequence
<220> FEATURE:
<223> OTHER INFORMATION: Synthetic

<400> SEQUENCE: 14
ataagatctt tagtgggtct tgtcacaaga tttgggctca actct      45

<210> SEQ ID NO 15
<211> LENGTH: 45
<212> TYPE: DNA
<213> ORGANISM: Artificial Sequence
<220> FEATURE:
<223> OTHER INFORMATION: Synthetic

<400> SEQUENCE: 15
ataagatctt taggtgtggg tcttgtcaca agatttgggc tcaac      45

<210> SEQ ID NO 16
<211> LENGTH: 672
<212> TYPE: DNA
<213> ORGANISM: Homo sapiens

<400> SEQUENCE: 16
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tgaagggccg attcaccatc tccagagaca cgccaagaa ctccctgtat      240
ctgcaaatga acagtctgag agctgaggat acggccgtat attactgtgc gaaagtctcg     300
taccttagca ccgcgtcctc ccttgactat tggggccaag ggaccctggt caccgtctcg     360
agtgctagct tcaagggccc atcggtcttc cccctggcac cctcctccaa gagcacctct     420
gggggcacag cggccctggg ctgcctggtc aaggactact ccccgaacc ggtgacggtg      480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gt                                                         672

<210> SEQ ID NO 17
<211> LENGTH: 645
<212> TYPE: DNA
<213> ORGANISM: Homo sapiens

<400> SEQUENCE: 17
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg gtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300

```
gggaccaagg tggaaatcaa acgaactgtg gcggcgccat ctgtcttcat cttcccgcca    360
tctgatgagc agttgaaatc tggaactgcc tctgttgtgt gcctgctgaa taacttctat    420
cctcgagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagattacga gaaacacaaa gtctacgcct gcgaagtcac ccatcagggc    600
ctgagctcgc ccgtcacaaa gagcttcaac aggggagagt gttag                    645
```

<210> SEQ ID NO 18
<211> LENGTH: 1510
<212> TYPE: DNA
<213> ORGANISM: Ogataea polymorpha

<400> SEQUENCE: 18

```
tcgacgcgga gaacgatctc ctcgagctgc tcgcggatca gcttgtggcc cggtaatgga     60
accaggccga cggcacgctc cttgcggacc acggtggctg cgagcccag tttgtgaacg     120 aggtcgttta aacgtcctg cgcaaagtcc agtgtcagat gaatgtcctc ctcggaccaa     180
ttcagcatgt tctcgagcag ccatctgtct ttggagtaga agcgtaatct ctgctcctcg     240
ttactgtacc ggaagaggta gtttgcctcg ccgcccataa tgaacaggtt ctctttctgg     300
tggcctgtga gcagcggga cgtctggacg cgtcgatga ggcccttgag gcgctcgtag      360
tacttgttcg cgtcgctgta gccggccgcg gtgacgatac ccacatagag gtccttggcc    420
attagtttga tgaggtgggg caggatgggc gactcggcat cgaaattttt gccgtcgtcg    480
tacagtgtga tgtcaccatc gaatgtaatg agctgcagct gcgatctcg gatggttttg     540 gaatggaaga accgcgacat ctccaacagc tgggccgtgt tgagaatgag ccggacgtcg    600
ttgaacgagg gggccacaag ccggcgtttg ctgatggcgc ggcgctcgtc ctcgatgtag    660 aaggccttt ccagaggcag tctcgtgaag aagctgccaa cgctcggaac cagctgcacg     720
agccgagaca attcgggggt gccggctttg gtcatttcaa tgttgtcgtc gatgaggagt    780
tcgaggtcgt ggaagatttc cgcgtagcgg cgtttttgcct cagagtttac catgaggtcg   840
tccactgcag agatgccgtt gctcttcacc gcgtacagga cgaacggcgt ggccagcagg    900
cccttgatcc attctatgag gccatctcga cggtgttcct tgagtgcgta ctccactctg    960
tagcgactgg acatctcgag actgggcttg ctgtgctgga tgcaccaatt aattgttgcc    1020
gcatgcatcc ttgcaccgca agttttttaaa acccactcgc tttagccgtc gcgtaaaact   1080
tgtgaatctg gcaactgagg gggttctgca gccgcaaccg aacttttcgc ttcgaggacg    1140
cagctggatg gtgtcatgtg aggctctgtt tgctggcgta gcctacaacg tgaccttgcc    1200
taaccggacg gcgctaccca ctgctgtctg tgcctgctac cagaaaatca ccagagcagc    1260
agagggccga tgtggcaact ggtggggtgt cggacaggct gtttctccac agtgcaaatg    1320
cgggtgaacc ggccagaaag taaattctta tgctaccgtg cagcgactcc gacatccca     1380 gttttgccc tacttgatca cagatggggt cagcgctgcc gctaagtgta cccaaccgtc     1440
cccacacggt ccatctataa atactgctgc cagtgcacgg tggtgacatc aatctaaagt    1500
acaaaaacaa                                                           1510
```

<210> SEQ ID NO 19
<211> LENGTH: 606
<212> TYPE: DNA
<213> ORGANISM: Ogataea polymorpha

<400> SEQUENCE: 19

```
gagacgtgga aggacatacc gcttttgaga agcgtgtttg aaaatagttc ttttctggt      60
ttatatcgtt tatgaagtga tgagatgaaa agctgaaata gcgagtatag gaaaatttaa    120
tgaaaattaa attaaatatt ttcttaggct attagtcacc ttcaaaatgc cggccgcttc    180
taagaacgtt gtcatgatcg acaactacga ctcgtttacc tggaacctgt acgagtacct    240
gtgtcaggag ggagccaatg tcgaggtttt caggaacgat cagatcacca ttccggagat    300
tgagcagctc aagccggacg ttgtggtgat atccctggt cctggccatc caagaacaga     360
ctcgggaata tctcgcgacg tgatcagcca ttttaaaggc aagattcctg tctttggtgt    420
ctgtatgggc cagcagtgta tcttcgagga gtttggcgga gacgtcgagt atgcgggcga    480
gattgtccat ggaaaaacgt ccactgttaa gcacgacaac aagggaatgt caaaaacgt     540
tccgcaagat gttgctgtca ccagatacca ctcgctggcc ggaacgctca agtcgcttcc    600
ggactg                                                                606
```

<210> SEQ ID NO 20
<211> LENGTH: 1340
<212> TYPE: DNA
<213> ORGANISM: Ogataea polymorpha

<400> SEQUENCE: 20

```
gagtccctga gtacgtaagc ggtttggtaa tacgaaataa aaagacagga atgagtaagt    60
ggatggtttt tcaattttc cggtaccggc gcaaaatagt tgcatcattt tgcaatcatg     120
agtaagaaca ttgtgcttct ccctggtgat cacgtgggcc ccgaggttgt tgcggaggcc    180
gtcaaggttc tcgaggctgt ctcgtcggca atcgcgtta agttcaactt ttccaagcac     240
ctgatcggcg tgcctcgat cgatgcttat ggggtgccat tgtccgacga ggccctcgaa     300
gccgccaaga aggctgacgc cgttttgctt ggagccgtcg aggacctaa gtggggaacc     360
ggctccgtgc gtcctgagca gggtctgttg aagatcagaa aagagctcaa cttgtacgcg    420
aacctgcgtc catgcagttt tgcttccgac gctcttctga agctatctcc actgaaatca    480
gaaatcgtca agggcactga ctttgttgtt gtgcgtgagt tggttggtgg aatctacttt    540
ggtgaccgca aggaggatgc cggcgacgga gttgccagcg cactgagag ctattctgtt     600
ccagaggtgc agagaatcac gagaatggcg gccttttggg cgctgcagag cgacccaccg    660
ctcccactgt ggtcgctgga caaagccaac gtgcttgcat cctcgcgttt gtggcggaag    720
actgttgagg agaccatcaa gaacgagttc ccgcagctga cggtgcagca ccagctgatc    780
gactcggcag ccatgatttt ggtcaagtcg ccaacgaaac tcaacggtgt cattgtcacc    840
aacaacatgt ttggcgacat catcagtgac gaggccagtg tgattcctgg gtctctgggc    900
ctgctgcctt ctgcctcgtt ggcgtctctg ccagacacaa acaaggcgtt tggtctttac    960
gagccctgcc acggctcggc gccagatttg ggcccgggca aggtcaatcc attggccaca    1020
attttgtctg ccgccatgat gctgaagctg tcgctggact tggtggatgc cggccgtgcg    1080
atcgagcagg ccgtcaagaa cgtcctggat gcaggtatca tgactgccga tttgggtgga    1140
agctcctcaa cacaggaagt tggtgatgct gttgcgcagg aggtggccaa gctactcaag    1200
aactaaataa gggagaaaaa aaagtaggat ctcgaataat tcctaaataa tcccaaaaat    1260
cctaaacacg cacgcctcac agatttatt tttttcgacg cgacgctcta ttgtttattt     1320
tttagctttt ccatgtcaac                                                 1340
```

<210> SEQ ID NO 21
<211> LENGTH: 255
<212> TYPE: DNA
<213> ORGANISM: Saccharomyces cerevisiae

<400> SEQUENCE: 21

```
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc catttccaa cagcacaaat      180 aacgggttat tgtttataaa tactactatt gccagcattg ctgctaaaga agaaggggta     240
tctctcgaga aaaga                                                      255
```

<210> SEQ ID NO 22
<211> LENGTH: 645
<212> TYPE: DNA
<213> ORGANISM: Homo sapiens

<400> SEQUENCE: 22

```
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa acgaactgtg gcggcgccat ctgtcttcat cttcccgcca     360
tctgatgagc agttgaaatc tggaactgcc tctgttgtgt gcctgctgaa taacttctat     420
cctcgagagg ccaaagtaca gtggaaggtg gataacgccc tccaatcggg taactcccag     480
gagagtgtca cagagcagga cagcaaggac agcacctaca gcctcagcag cacccctgacg     540 ctgagcaaag cagattacga gaaacacaaa gtctacgcct gcgaagtcac ccatcagggc     600
ctgagctcgc ccgtcacaaa gagcttcaac aggggagagt gttag                     645
```

<210> SEQ ID NO 23
<211> LENGTH: 1356
<212> TYPE: DNA
<213> ORGANISM: Homo sapiens

<400> SEQUENCE: 23

```
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tgagggccg attcaccatc tccagagaca cgccaagaa ctccctgtat      240 ctgcaaatga acagtctgag agctgaggat acggccgtat attactgtgc gaaagtctcg     300
taccttagca ccgcgtcctc ccttgactat tggggccaag gaccctggt caccgtctcg     360 agtgctagct tcaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
```

```
ggaccgtcag tcttcctctt ccccccaaaa cccaaggaca ccctcatgat ctcccggacc      780
cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga gaaaaccatc     1020
tccaaagcca agggcagccc cgagaaccac aggtgtacac cctgcccccc atcccgggag     1080
gagatgacca agaaccaggt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tatagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaatga                               1356
```

<210> SEQ ID NO 24
<211> LENGTH: 44
<212> TYPE: DNA
<213> ORGANISM: Artificial Sequence
<220> FEATURE:
<223> OTHER INFORMATION: Synthetic

<400> SEQUENCE: 24

```
aagcttgcgg ccgcggatcc actagtagat cttctagaga attc                        44
```

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25

```
ataaaagctt gagtccctga gtacgtaagc                                        30
```

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26

```
tataaagctt gttgacatgg aaaagctaaa aaata                                  35
```

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27

```
ataaggatcc tcgacgcgga gaacgatctc                                        30
```

<210> SEQ ID NO 28
<211> LENGTH: 35
<212> TYPE: DNA
<213> ORGANISM: Artificial Sequence
<220> FEATURE:
<223> OTHER INFORMATION: Synthetic

<400> SEQUENCE: 28
tataggatcc ttgtttttgt actttagatt gatgt                                35

<210> SEQ ID NO 29
<211> LENGTH: 33
<212> TYPE: DNA
<213> ORGANISM: Artificial Sequence
<220> FEATURE:
<223> OTHER INFORMATION: Synthetic

<400> SEQUENCE: 29
ataaactagt atgagatttc ttcaatttt tac                                  33

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
tataagatct tttctcgaga gataccctt ct                                   32

<210> SEQ ID NO 31
<211> LENGTH: 33
<212> TYPE: DNA
<213> ORGANISM: Artificial Sequence
<220> FEATURE:
<223> OTHER INFORMATION: Synthetic

<400> SEQUENCE: 31
ataatctaga gagacgtgga aggacatacc gct                                 33

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
tatatctaga cagtccggaa gcgacttgag cgt                                 33

<210> SEQ ID NO 33
<211> LENGTH: 33
<212> TYPE: DNA
<213> ORGANISM: Artificial Sequence
<220> FEATURE:
<223> OTHER INFORMATION: Synthetic

<400> SEQUENCE: 33
ataaagatct gacatccaga tgacccagtc tcc                                 33

<210> SEQ ID NO 34
<211> LENGTH: 32
<212> TYPE: DNA
<213> ORGANISM: Artificial Sequence
<220> FEATURE:
<223> OTHER INFORMATION: Synthetic

<400> SEQUENCE: 34
tataagatct ctaacactct ccctgttga ag                                   32

<210> SEQ ID NO 35
<211> LENGTH: 30
<212> TYPE: DNA

```
<213> ORGANISM: Artificial Sequence
<220> FEATURE:
<223> OTHER INFORMATION: Synthetic

<400> SEQUENCE: 35
ataaagatct gaggtgcagc tggtggagtc                                        30

<210> SEQ ID NO 36
<211> LENGTH: 36
<212> TYPE: DNA
<213> ORGANISM: Artificial Sequence
<220> FEATURE:
<223> OTHER INFORMATION: Synthetic

<400> SEQUENCE: 36
tataagatct ttaacaagat ttgggctcaa ctctct                                 36

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
ataagaattc tcgacgcgga gaacgatctc                                        30

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38
tatagaattc tatttcagct tttcatctca tca                                    33

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
tataagatct ttaaccacaa gatttgggct caactctct                              39

<210> SEQ ID NO 40
<211> LENGTH: 39
<212> TYPE: DNA
<213> ORGANISM: Artificial Sequence
<220> FEATURE:
<223> OTHER INFORMATION: Synthetic

<400> SEQUENCE: 40
tataagatct ttaggcacaa gatttgggct caactctct                              39

<210> SEQ ID NO 41
<211> LENGTH: 39
<212> TYPE: DNA
<213> ORGANISM: Artificial Sequence
<220> FEATURE:
<223> OTHER INFORMATION: Synthetic

<400> SEQUENCE: 41
tataagatct ttaaacacaa gatttgggct caactctct                              39
```

<210> SEQ ID NO 42
<211> LENGTH: 39
<212> TYPE: DNA
<213> ORGANISM: Artificial Sequence
<220> FEATURE:
<223> OTHER INFORMATION: Synthetic

<400> SEQUENCE: 42
tataagatct ttacagacaa gatttgggct caactctct						39

<210> SEQ ID NO 43
<211> LENGTH: 39
<212> TYPE: DNA
<213> ORGANISM: Artificial Sequence
<220> FEATURE:
<223> OTHER INFORMATION: Synthetic

<400> SEQUENCE: 43
tataagatct ttagatacaa gatttgggct caactctct						39

<210> SEQ ID NO 44
<211> LENGTH: 39
<212> TYPE: DNA
<213> ORGANISM: Artificial Sequence
<220> FEATURE:
<223> OTHER INFORMATION: Synthetic

<400> SEQUENCE: 44
tataagatct ttagcaacaa gatttgggct caactctct						39

<210> SEQ ID NO 45
<211> LENGTH: 39
<212> TYPE: DNA
<213> ORGANISM: Artificial Sequence
<220> FEATURE:
<223> OTHER INFORMATION: Synthetic

<400> SEQUENCE: 45
tataagatct ttacatacaa gatttgggct caactctct						39

<210> SEQ ID NO 46
<211> LENGTH: 39
<212> TYPE: DNA
<213> ORGANISM: Artificial Sequence
<220> FEATURE:
<223> OTHER INFORMATION: Synthetic

<400> SEQUENCE: 46
tataagatct ttaggaacaa gatttgggct caactctct						39

<210> SEQ ID NO 47
<211> LENGTH: 39
<212> TYPE: DNA
<213> ORGANISM: Artificial Sequence
<220> FEATURE:
<223> OTHER INFORMATION: Synthetic

<400> SEQUENCE: 47
tataagatct ttaggtacaa gatttgggct caactctct						39

<210> SEQ ID NO 48
<211> LENGTH: 39
<212> TYPE: DNA
<213> ORGANISM: Artificial Sequence
<220> FEATURE:

<223> OTHER INFORMATION: Synthetic

<400> SEQUENCE: 48
tataagatct ttagtaacaa gatttgggct caactctct                          39

<210> SEQ ID NO 49
<211> LENGTH: 39
<212> TYPE: DNA
<213> ORGANISM: Artificial Sequence
<220> FEATURE:
<223> OTHER INFORMATION: Synthetic

<400> SEQUENCE: 49
tataagatct ttagaaacaa gatttgggct caactctct                          39

<210> SEQ ID NO 50
<211> LENGTH: 39
<212> TYPE: DNA
<213> ORGANISM: Artificial Sequence
<220> FEATURE:
<223> OTHER INFORMATION: Synthetic

<400> SEQUENCE: 50
tataagatct ttaccaacaa gatttgggct caactctct                          39

<210> SEQ ID NO 51
<211> LENGTH: 39
<212> TYPE: DNA
<213> ORGANISM: Artificial Sequence
<220> FEATURE:
<223> OTHER INFORMATION: Synthetic

<400> SEQUENCE: 51
tataagatct ttaaggacaa gatttgggct caactctct                          39

<210> SEQ ID NO 52
<211> LENGTH: 39
<212> TYPE: DNA
<213> ORGANISM: Artificial Sequence
<220> FEATURE:
<223> OTHER INFORMATION: Synthetic

<400> SEQUENCE: 52
tataagatct ttactcacaa gatttgggct caactctct                          39

<210> SEQ ID NO 53
<211> LENGTH: 39
<212> TYPE: DNA
<213> ORGANISM: Artificial Sequence
<220> FEATURE:
<223> OTHER INFORMATION: Synthetic

<400> SEQUENCE: 53
tataagatct ttagttacaa gatttgggct caactctct                          39

<210> SEQ ID NO 54
<211> LENGTH: 39
<212> TYPE: DNA
<213> ORGANISM: Artificial Sequence
<220> FEATURE:
<223> OTHER INFORMATION: Synthetic

<400> SEQUENCE: 54
tataagatct ttactgacaa gatttgggct caactctct                          39

```
<210> SEQ ID NO 55
<211> LENGTH: 39
<212> TYPE: DNA
<213> ORGANISM: Artificial Sequence
<220> FEATURE:
<223> OTHER INFORMATION: Synthetic

<400> SEQUENCE: 55
tataagatct ttacttacaa gatttgggct caactctct                              39

<210> SEQ ID NO 56
<211> LENGTH: 39
<212> TYPE: DNA
<213> ORGANISM: Artificial Sequence
<220> FEATURE:
<223> OTHER INFORMATION: Synthetic

<400> SEQUENCE: 56
tataagatct ttatctacaa gatttgggct caactctct                              39

<210> SEQ ID NO 57
<211> LENGTH: 39
<212> TYPE: DNA
<213> ORGANISM: Artificial Sequence
<220> FEATURE:
<223> OTHER INFORMATION: Synthetic

<400> SEQUENCE: 57
tataagatct ttagtgacaa gatttgggct caactctct                              39

<210> SEQ ID NO 58
<211> LENGTH: 35
<212> TYPE: DNA
<213> ORGANISM: Artificial Sequence
<220> FEATURE:
<223> OTHER INFORMATION: Synthetic

<400> SEQUENCE: 58
tataagatct ctagtcacac tctcccctgt tgaag                                  35

<210> SEQ ID NO 59
<211> LENGTH: 645
<212> TYPE: DNA
<213> ORGANISM: Homo sapiens

<400> SEQUENCE: 59
gacatccttc tgacccaatc tccagccatc ctttctgtca gccctggaga gagagtgtct       60
tttagctgta gagcttctca gttcgttggc agctctatcc actggtatca acagagaaca      120
aacggaagcc caagacttct gatcaagtac gcatctgaaa gcatgtctgg cattcctagc      180
agattttctg gaagcggctc tggaactgat ttcacactga gcatcaatac cgtcgagtct      240
gaagacatcg ccgattacta ttgtcaacag agccattctt ggccatttac attcggcagc      300
ggaactaacc tggaggtgaa agaacagttg ctgcaccctt ctgtctttat tttcccacct      360
agcgatgaac aactgaagtc tggaaccgcc agcgtggttt gtctgcttaa taacttttac      420
ccaagagagg ctaaagtcca gtggaaggtg ataatgcac  tgcaatctgg caacagccag      480
gaatctgtga cagagcaaga cagcaaagat tctacttaca gcctgtctag cacacttacc      540
ctgtctaaag ccgactacga aaagcacaaa gtgtatgctt gtgaggttac acatcagggc      600
ctgagctctc ctgtcactaa gagcttcaat agaggcgaat gttag                      645

<210> SEQ ID NO 60
```

<211> LENGTH: 672
<212> TYPE: DNA
<213> ORGANISM: Homo sapiens

<400> SEQUENCE: 60

```
gaggttaaac tggaagagtc tggcggaggc cttgtccagc caggcggaag catgaagctg      60
tcttgtgtgg ccagcggctt catctttct aaccactgga tgaattgggt tagacaaagc     120
cctgaaaaag gcctggagtg ggtcgcagaa atcagatcta agagcattaa ctctgccaca    180
cattacgctg agagcgtgaa aggcagattc accatcagca gagatgactc taagagcgca    240
gtttacctgc agatgacaga tcttagaact gaagacacag cgtctacta ttgtagcaga     300
aattactatg gctctaccta cgattattgg ggacaaggca caactctgac agtgagcgca    360
gcctctttta aaggcccaag cgttttccct ctggctccat ctagcaagtc tacaagcggc    420
ggaaccgcag cccttggctg tctggtcaaa gactactttc ctgagccagt gacagtttct    480
tggaacagcg gcgctctgac ttctggagtc cacacattcc ctgcagtgct tcagagctct    540
ggcctgtaca gcctttctag cgttgtcacc gtgccatcta gctctctggg aacacaaact    600
tacatctgta atgtgaacca taagcctagc aatacaaaag ttgataagaa agtcgaacca    660
aagtcttgtt aa                                                        672
```

<210> SEQ ID NO 61
<211> LENGTH: 34
<212> TYPE: DNA
<213> ORGANISM: Artificial Sequence
<220> FEATURE:
<223> OTHER INFORMATION: Synthetic

<400> SEQUENCE: 61

```
ataaagatct gacatccttc tgacccaatc tcca                                 34
```

<210> SEQ ID NO 62
<211> LENGTH: 33
<212> TYPE: DNA
<213> ORGANISM: Artificial Sequence
<220> FEATURE:
<223> OTHER INFORMATION: Synthetic

<400> SEQUENCE: 62

```
tataagatct ctaacattcg cctctattga agc                                  33
```

<210> SEQ ID NO 63
<211> LENGTH: 32
<212> TYPE: DNA
<213> ORGANISM: Artificial Sequence
<220> FEATURE:
<223> OTHER INFORMATION: Synthetic

<400> SEQUENCE: 63

```
ataaagatct gaggttaaac tggaagagtc tg                                   32
```

<210> SEQ ID NO 64
<211> LENGTH: 34
<212> TYPE: DNA
<213> ORGANISM: Artificial Sequence
<220> FEATURE:
<223> OTHER INFORMATION: Synthetic

<400> SEQUENCE: 64

```
tataagatct ttaacaagac tttggttcga cttt                                 34
```

<210> SEQ ID NO 65
<211> LENGTH: 37
<212> TYPE: DNA
<213> ORGANISM: Artificial Sequence
<220> FEATURE:
<223> OTHER INFORMATION: Synthetic

<400> SEQUENCE: 65
tataagatct ttagtcacaa gactttggtt cgactttt      37

<210> SEQ ID NO 66
<211> LENGTH: 1091
<212> TYPE: DNA
<213> ORGANISM: Artificial Sequence
<220> FEATURE:
<223> OTHER INFORMATION: Synthetic

<400> SEQUENCE: 66
gctatacaga gctttatatc accttactga acgctagagt agacccaatt cccggctcac      60 accacccta catgcagagc taaccaataa ggtaattaat taacactata tagctcgtgg      120
tgaacactgg cccggagtag tcatacgtgt aggtttttgg cgtgatgaaa atcaggtggc      180
gcacgacttt tcgtaaagtt cgggagggag tgctgcaaac ggtatataag gaccagtttt      240
tctcgcacat tatcaattgc tctttagtac aaagataata tagaaaccat atgattgaac      300
aagatggatt gcacgcaggt tctccggccg cttgggtgga gaggctattc ggctatgact      360
gggcacaaca gacaatcggc tgctctgatg ccgccgtgtt ccggctgtca gcgcaggggc      420
gcccggttct ttttgtcaag accgacctgt ccggtgccct gaatgaactg caggacgagg      480
cagcgcggct atcgtggctg gccacgacgg gcgttccttg cgcagctgtg ctcgacgttg      540
tcactgaagc gggaagggac tggctgctat tgggcgaagt gccggggcag gatctcctgt      600
catctcacct tgctcctgcc gagaaagtat ccatcatggc tgatgcaatg cggcggctgc      660
atacgcttga tccggctacc tgcccattcg accaccaagc gaaacatcgc atcgagcgag      720
cacgtactcg gatggaagcc ggtcttgtcg atcaggatga tctggacgaa gagcatcagg      780
ggctcgcgcc agccgaactg ttcgccaggc tcaaggcgcg catgcccgac ggcgaggatc      840
tcgtcgtgac ccatggcgat gcctgcttgc cgaatatcat ggtggaaaat ggccgctttt      900
ctggattcat cgactgtggc cggctgggtg tggcggaccg ctatcaggac atagcgttgg      960
ctacccgtga tattgctgaa gagcttggcg gcgaatgggc tgaccgcttc ctcgtgcttt     1020
acggtatcgc cgctcccgat tcgcagcgca tcgccttcta tcgccttctt gacgagttct     1080
tctgagcggg a     1091

<210> SEQ ID NO 67
<211> LENGTH: 34
<212> TYPE: DNA
<213> ORGANISM: Artificial Sequence
<220> FEATURE:
<223> OTHER INFORMATION: Synthetic

<400> SEQUENCE: 67
ataaaagctt gctatacaga gctttatatc acct      34

<210> SEQ ID NO 68
<211> LENGTH: 33
<212> TYPE: DNA
<213> ORGANISM: Artificial Sequence
<220> FEATURE:
<223> OTHER INFORMATION: Synthetic

<400> SEQUENCE: 68
tataaagctt tcccgctcag aagaactcgt caa                               33

<210> SEQ ID NO 69
<211> LENGTH: 10
<212> TYPE: PRT
<213> ORGANISM: Artificial Sequence
<220> FEATURE:
<223> OTHER INFORMATION: Synthetic

<400> SEQUENCE: 69

Asp Lys Thr His Thr Asp Lys Thr His Thr
1               5                   10

<210> SEQ ID NO 70
<211> LENGTH: 30
<212> TYPE: DNA
<213> ORGANISM: Artificial Sequence
<220> FEATURE:
<223> OTHER INFORMATION: Synthetic

<400> SEQUENCE: 70
gacaagaccc acaccgacaa gacccacacc                                  30

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
atagatcttt aggtgtgggt cttgtcggtg tgggtcttgt cacaa                 45

<210> SEQ ID NO 72
<211> LENGTH: 5
<212> TYPE: PRT
<213> ORGANISM: Artificial Sequence
<220> FEATURE:
<223> OTHER INFORMATION: Synthetic

<400> SEQUENCE: 72

Asp Lys Thr His Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic

<400> SEQUENCE: 73

Asp Lys Thr His Thr Cys Ala Ala
1               5

<210> SEQ ID NO 74
<211> LENGTH: 30
<212> TYPE: PRT
<213> ORGANISM: Artificial Sequence
<220> FEATURE:
<223> OTHER INFORMATION: Synthetic

<400> SEQUENCE: 74

Gly Gly Gly Gly Ser Met Val Ser Lys Gly Glu Glu Leu Phe Thr Gly
1               5                   10                  15

```
Val Val Pro Ile Leu Val Glu Leu Asp Gly Asp Val Asn Gly
            20                  25                  30

<210> SEQ ID NO 75
<211> LENGTH: 90
<212> TYPE: DNA
<213> ORGANISM: Artificial Sequence
<220> FEATURE:
<223> OTHER INFORMATION: Synthetic

<400> SEQUENCE: 75
ggaggtggcg gatccatggt gagcaagggc gaggagctgt tcaccggggt ggtgcccatc      60
ctggtcgagc tggacggcga cgtaaacggc                                      90

<210> SEQ ID NO 76
<211> LENGTH: 31
<212> TYPE: DNA
<213> ORGANISM: Artificial Sequence
<220> FEATURE:
<223> OTHER INFORMATION: Synthetic

<400> SEQUENCE: 76
ataaagatct atggtgagca agggcgagga g                                    31

<210> SEQ ID NO 77
<211> LENGTH: 34
<212> TYPE: DNA
<213> ORGANISM: Artificial Sequence
<220> FEATURE:
<223> OTHER INFORMATION: Synthetic

<400> SEQUENCE: 77
tataggatcc ttagccgttt acgtcgccgt ccag                                 34

<210> SEQ ID NO 78
<211> LENGTH: 40
<212> TYPE: DNA
<213> ORGANISM: Artificial Sequence
<220> FEATURE:
<223> OTHER INFORMATION: Synthetic

<400> SEQUENCE: 78
tataggatcc gccacctcca caagatttgg gctcaactct                           40
```

FD CHAIN GENE OR L CHAIN GENE CAPABLE OF INCREASING SECRETION AMOUNT OF FAB-TYPE ANTIBODY

The present application is a continuation-in-part application of PCT/JP2014/060941 filed on Apr. 17, 2014 and claims priorities under 35 U.S.C. § 119 of Japanese Patent Application No. 92862/2013 filed on Apr. 25, 2013 and Japanese Patent Application No. 221703/2013 filed on Oct. 25, 2013, the content of which are herein incorporated by reference in their entirety.

REFERENCE TO SEQUENCE LISTING SUBMITTED VIA EFS-WEB

This application includes an electronically submitted sequence listing in .txt format. The .txt file contains a sequence listing entitled "2015-12-29 2870-0619PUS1_ST25.txt" created on Dec. 29, 2015 and is 30,570 bytes bytes in size. The sequence listing contained in this .txt file is part of the specification and is hereby incorporated by reference herein in its entirety.

TECHNICAL FIELD

The present invention relates to a gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain or L chain of an antibody. The present invention also relates to a recombinant vector comprising the aforementioned gene, a transformant having the aforementioned recombinant vector, a method for producing a Fab-type antibody using the aforementioned transformant, and a Fab-type antibody having an amino acid or an amino acid sequence capable of increasing the secretion amount of the Fab-type antibody at the C-terminus of the amino acid sequence of the Fd chain and/or L chain of an antibody.

BACKGROUND ART

In order to produce a protein using genetic recombination technology, a host suitable for the expression of the protein is used. Examples of the host used to produce proteins include: animal cells such as CHO cells; insects such as silkworm and insect cells; animals such as chicken or bovine; and microorganisms such as *Escherichia coli* or yeast. Among these, yeast enables a large-scale high-density culture using an inexpensive medium, and it is able to produce proteins at low costs. Moreover, if a secretory signal peptide or the like is used, it is possible to carry out secretory production of proteins into a culture solution, and thus, it becomes easy to purity the proteins. As proteins produced using the aforementioned host, low-molecular-weight antibodies such as scFv and a Fab-type antibody that are next-generation protein pharmaceutical products have attracted attention. However, when such a low-molecular-weight antibody is allowed to express in yeast used as a host, there is a problem regarding low productivity of the antibody, and there is also a fear that a carbon source may have an influence on the product.

It has been reported that, as a means for solving the aforementioned problems, methanol-assimilating yeast, such as yeast of the genus *Komagataella*, yeast of the genus *Ogataea*, and yeast of the genus *Candida*, is used as a host for avoiding the influence of such a carbon source on the product. Moreover, in order to improve the productivity of proteins, a method for producing a Fab-type antibody, which comprises disposing a nucleotide sequence encoding the Fab-type antibody downstream of a promoter such as methanol oxidase or alcohol oxidase that has an activity several times higher than a common promoter, has been reported (Non Patent Literature 1). However, when a protein having a higher-order structure, such as a Fab-type antibody, is allowed to express using a strong promoter as described above, there is a problem that Fab-type antibodies whose conformations are not correctly folded are accumulated in the endoplasmic reticulum, and stress called "endoplasmic reticulum stress" is given to a cell mass.

As stated above, in order to produce, at low costs, a low-molecular-weight antibody such as a Fab-type antibody using yeast as a host, a method of using a promoter having a higher activity than usual has been known, but this method may cause endoplasmic reticulum stress. Accordingly, such a method of using a promoter having a higher activity than usual cannot be considered to be efficient from the viewpoint of high productivity, and thus, the problem has not yet been solved.

PRIOR ART LITERATURES

Non Patent Literature

Non Patent Literature 1: Biotechnology and Bioengineering, Vol. 94, 353-361, 2006

SUMMARY OF INVENTION

Problem to be Solved by the Invention

It is an object of the present invention to provide a method for producing a low-molecular-weight antibody such as a Fab-type antibody, using yeast as a host, wherein the method is able to produce the low-molecular-weight antibody with high productivity. Specifically, it is the object of the present invention to provide a method capable of producing a low-molecular-weight antibody such as a Fab-type antibody with high productivity, using yeast as a host and without using a promoter having a high activity.

Means for Solving the Object

As a result of intensive studies directed towards achieving the aforementioned object, the present inventors have found that a nucleotide sequence encoding 1 to 10 amino acid residues is ligated to the 3'-terminus of a nucleotide sequence encoding the amino acid sequence of an Fd chain or an L chain, and this ligate is then allowed to express in yeast, so that the productivity of a Fab-type antibody can be improved, thereby completing the present invention.

Thus, the present invention provides the following invention.

(1) A gene comprising a nucleotide sequence encoding an amino acid or an amino acid sequence capable of increasing a secretion amount of Fab-type antibody at 3'-terminus of a nucleotide sequence encoding an amino acid sequence of Fd chain or L chain of an antibody.

(2) The gene according to (1), wherein the amino acid or the amino acid sequence capable of increasing the secretion amount of Fab-type antibody consists of 1 to 30 amino acids.

(3) The gene according to (1) or (2), wherein the amino acid or the amino acid sequence capable of increasing the secretion amount of a Fab-type antibody is any one of Asp, Gly, Ala, Val, Leu, Ile, Cys, Met, Ser, Thr, Tyr, Phe, Trp, Pro, Glu, Asn, Gln, Lys, Arg, His, Asp-Lys, Asp-Lys-Thr, Asp-Lys-Thr-His (SEQ ID NO: 1), Asp-Lys-Thr-His-Thr-Asp-Lys-Thr-His-Thr (SEQ ID NO: 69), and Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO: 74).

(4) A recombinant vector comprising the gene according to any of (1) to (3).

(5) The recombinant vector according to (4), which is any of the following (a) to (c):

(a) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene of an antibody;

(b) a recombinant vector, which comprises an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody, and a Fd chain gene of an antibody; and (c) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody.

(6) A combination of recombinant vectors, which is any of the following (A) to (C):

(A) a combination of a recombinant vector comprising an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and a recombinant vector comprising the L chain gene of an antibody;

(B) a combination of a recombinant vector comprising an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody, and a recombinant vector comprising the Fd chain gene of an antibody; and (C) a combination of a recombinant vector comprising an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and a recombinant vector comprising an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody.

(7) A transformant obtained by transforming a host with the recombinant vector according to (4) or (5), or with the combination of recombinant vectors according to (6).

(8) The transformant according to (7), wherein the host is yeast.

(9) The transformant according to (7) or (8), wherein the yeast is yeast of the genus *Ogataea* or the genus *Komagataella*.

(10) The transformant according to (9), wherein the yeast of the genus *Ogataea* or the genus *Komagataella* is *Ogataea polymorpha* or *Komagataella pastoris*.

(11) The transformant according to any of (7) to (10), wherein when the transformant is cultured to produce a Fab-type antibody, the secretory production amount of a Fab-type antibody in a culture supernatant is 2.0 mg/L or more.

(12) A method for producing a Fab-type antibody, which comprises a step of culturing the transformant according to any of (7) to (11) and then recovering a Fab-type antibody.

(13) A Fab-type antibody having an amino acid or an amino acid sequence capable of increasing the secretion amount of the Fab-type antibody at the C-terminus of the amino acid sequence of the Fd chain and/or L chain of an antibody.

(14) The Fab-type antibody according to (13), wherein the amino acid or the amino acid sequence capable of increasing the secretion amount of the Fab-type antibody consist of 1 to 30 amino acids.

(15) The Fab-type antibody according to (13) or (14), wherein the amino acid or the amino acid sequence capable of increasing the secretion amount of the Fab-type antibody is any one of Asp, Gly, Ala, Val, Leu, Ile, Cys, Met, Ser, Thr, Tyr, Phe, Trp, Pro, Glu, Asn, Gln, Lys, Arg, His, Asp-Lys, Asp-Lys-Thr, Asp-Lys-Thr-His (SEQ ID NO: 1), Asp-Lys-Thr-His-Thr-Asp-Lys-Thr-His-Thr (SEQ ID NO: 69), and Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO: 74).

(16) An antibody drug conjugate wherein a growth inhibitor or a cytotoxic substance is conjugated to the Fab-type antibody of any one of (13) to (15).

Advantageous Effects of Invention

According to the present invention, only by ligating a nucleotide sequence encoding an amino acid or an amino acid sequence capable of increasing the secretion amount of a Fab-type antibody to the 3'-terminus of a nucleotide sequence encoding the amino acid sequence of the Fd chain or L chain of an antibody, the productivity of the Fab-type antibody can be improved. According to the present invention, there is no fear that endoplasmic reticulum stress should be given to a cell mass, since it is not necessary to use a promoter having a higher activity than usual in the present invention. In addition, since yeast that can be used in a high-density culture can be used as a host in the method for producing a Fab-type antibody according to the present invention, the production cost of antibodies can be reduced. The present invention is useful for the development of antibody drugs.

EMBODIMENTS FOR CARRYING OUT THE INVENTION

Hereinafter, the embodiments of the present invention will be described more in detail.

The Fd chain of an antibody in the present invention means a portion obtained by eliminating a hinge portion and an Fc region from the H chain of an IgG antibody, wherein the portion ranges from the N-terminus of the H chain to a cysteine residue binding to the cysteine at the C-terminus of an L chain via an S—S bond.

The nucleotide sequence encoding the amino acid sequence of an Fd chain or an L chain in the present invention is not particularly limited, as long as it is a DNA fragment encoding the amino acid sequence of an Fd chain or an L chain.

The type of an antibody, from which the Fd chain or L chain used in the present invention is derived, is not particularly limited. Examples of such an antibody include a human antibody, a humanized antibody, a mouse antibody, a dog antibody, a cat antibody, a horse antibody, a bovine antibody, a swine antibody, a chicken antibody, and a chimeric antibody formed by fusing these antibodies.

The antigen, to which the aforementioned antibody as an origin of the Fd chain or L chain used in the present invention binds, is not particularly limited, either. Preferred examples of the antigen include antigens known as targets of drug discovery, such as CD20, HER2, IL2R, CD33, CD52, EGFR, VEGF, CD3, CD25, TNFα, CD11, IgE, CD2, α4 integrin, CD80, CD86, IL6R, C5a, GPIIb/IIIa, RSVF Protein, VEGF-A and GM-CSF.

A specific example of the nucleotide sequence encoding the amino acid sequence of an Fd chain is a nucleotide sequence shown in SEQ ID NO: 16 or SEQ ID NO: 60.

The L chain gene in the present invention may be a gene, in which a Fab-type antibody is produced when the L chain gene is allowed to express together with the Fd chain gene. It is a nucleotide sequence encoding the amino acid sequence of the L chain of an IgG antibody. A specific example of the L chain gene is a nucleotide sequence shown in SEQ ID NO: 17 or SEQ ID NO: 59.

The gene of the present invention comprises a nucleotide sequence encoding an amino acid or an amino acid sequence capable of increasing the secretion amount of a Fab-type antibody at the 3'-terminus of a nucleotide sequence encoding the amino acid sequence of the Fd chain or L chain of an antibody.

The amino acid or the amino acid sequence capable of increasing the secretion amount of a Fab-type antibody is not particularly limited, as long as it exhibits an action to increase the secretion amount of a Fab-type antibody. The number of amino acids is not particularly limited, either. The number of amino acids is preferably 1 to 30, and more preferably 1 to 10 or 1 to 5.

A specific example of the amino acid or the amino acid sequence capable of increasing the secretion amount of a Fab-type antibody is any one of Asp, Gly, Ala, Val, Leu, Ile, Cys, Met, Ser, Thr, Tyr, Phe, Trp, Pro, Glu, Asn, Gln, Lys, Arg, His, Asp-Lys, Asp-Lys-Thr, Asp-Lys-Thr-His (SEQ ID NO: 1), Asp-Lys-Thr-His-Thr (SEQ ID NO: 2), Asp-Lys-Thr-His-Thr-Asp-Lys-Thr-His-Thr (SEQ ID NO: 69), and Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO: 74). In addition, several amino acids or amino acid sequences may be selected from the above-described amino acids or amino acid sequences, and they may be used in combination. However, an aspect, in which the gene comprises a nucleotide sequence encoding a histidine tag consisting of a multiple number (e.g., approximately 6 to 10) of His at the 3'-terminus of a nucleotide sequence encoding the amino acid sequence of the Fd chain or L chain of an antibody, is excluded from the present invention. Likewise, an embodiment in which the gene comprises a nucleotide sequence encoding Asp-Lys-Thr-His-Thr (SEQ ID NO: 2), Asp-Lys-Thr-His-Leu (SEQ ID NO: 72) or Asp-Lys-Thr-His-Thr-Cys-Ala-Ala (SEQ ID NO: 73) at the 3'-terminus of a nucleotide sequence encoding the amino acid sequence of the Fd chain or L chain of an antibody, is also excluded from the present invention.

The above-described nucleotide sequence encoding an amino acid or an amino acid sequence capable of increasing the secretion amount of a Fab-type antibody consists of a combination of nucleotide sequences each encoding individual amino acid codons. Each amino acid codon can be arbitrarily selected from codons that can be used in a host for expressing an Fd chain gene or an L chain gene. Specifically, in the case of Asp, the amino acid codon is gac; in the case of Asp-Lys, it is gacaag; in the case of Asp-Lys-Thr, it is gacaagacc; and in the case of Asp-Lys-Thr-His (SEQ ID NO: 1), it is gacaagacccac (SEQ ID NO: 3). Moreover, in the case of Asp-Lys-Thr-His-Thr (SEQ ID NO: 2), it is the nucleotide sequence of gacaagacccacacc (SEQ ID NO: 4); in the case of Asp-Lys-Thr-His-Thr-Asp-Lys-Thr-His-Thr (SEQ ID NO: 69), it is gacaagacccacaccgacaagacccacacc (SEQ ID NO: 70); and in the case of Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO: 74), it is ggaggtggcggatccatggtgagcaagggcgaggagctgttcaccggggtggtgcccatcctggtcgagctggacggcg acgtaaacggc (SEQ ID NO: 75). However, the examples are not limited thereto.

The aforementioned Asp, Gly, Ala, Val, Leu, Ile, Cys, Met, Ser, Thr, Tyr, Phe, Trp, Pro, Glu, Asn, Gln, Lys, Arg and His indicate an aspartic acid residue, a glycine residue, an alanine residue, a valine residue, a leucine residue, an isoleucine residue, a cysteine residue, a methionine residue, a serine residue, a threonine residue, a tyrosine residue, a phenylalanine residue, a tryptophan residue, a proline residue, a glutamic acid residue, an asparagine residue, a glutamine residue, a lysine residue, an arginine residue and a histidine residue, respectively. In addition, T representing a nucleotide indicates thymine, A indicates adenine, G indicates guanine, and C indicates cytosine.

The gene may comprise any one of gac, gacaag, gacaagacc, gacaagacccac (SEQ ID NO: 3) and gacaagacccacacc (SEQ ID NO: 4) at the 3'-terminus of a nucleotide sequence encoding a protein having the amino acid sequence of the Fd chain as mentioned above, and may further comprise a nucleotide sequence consisting of taa, tga and tag as termination codons at the 3'-terminus thereof.

SEQ ID NO: 5 is a gene, in which the nucleotide sequence gac and the nucleotide sequence of the termination codon taa are ligated to the 3'-terminus of the nucleotide sequence shown in SEQ ID NO: 16.

SEQ ID NO: 6 is a gene, in which the nucleotide sequence gacaag and the nucleotide sequence of the termination codon taa are ligated to the 3'-terminus of the nucleotide sequence shown in SEQ ID NO: 16.

SEQ ID NO: 7 is a gene, in which the nucleotide sequence gacaagacc and the nucleotide sequence of the termination codon taa are ligated to the 3'-terminus of the nucleotide sequence shown in SEQ ID NO: 16.

SEQ ID NO: 8 is a gene, in which the nucleotide sequence gacaagacccac (SEQ ID NO: 3) and the nucleotide sequence of the termination codon taa are ligated to the 3'-terminus of the nucleotide sequence shown in SEQ ID NO: 16.

SEQ ID NO: 9 is a gene, in which the nucleotide sequence gacaagacccacacc (SEQ ID NO: 4) and the nucleotide sequence of the termination codon taa are ligated to the 3'-terminus of the nucleotide sequence shown in SEQ ID NO: 16.

The recombinant vector in the present invention means a nucleic acid molecule having the function of allowing the above-described Fd chain gene to express in the transformed host cell. The recombinant vector may have a homologous region for incorporation, a selection marker gene such as an auxotrophic complementary gene or a drug resistance gene, an autonomously replicating sequence, and the like, in addition to an expression cassette.

In the present invention, after completion of the transformation of a host with a vector, the vector may be in a state in which it is incorporated into the chromosome of the transformant, or in a state in which it is present in the form of an autonomously replicating vector. Examples of such an autonomously replicating vector include a YEp vector, a YRp vector, and a YCp vector. In the case of the genus *Komagataella*, examples of the available vector include pPICHOLI, pHIP, pHRP, and pHARS. However, the examples are not particularly limited thereto.

The "expression cassette" according to the present invention is composed of a promoter and a protein gene of interest to be expressed. The expression cassette may also comprise a terminator gene, and for example, it can be constructed by using a plasmid such as pUC19, or can also be produced by a PCR method.

The homologous region for incorporation in the present invention means a region where the recombinant vector of the present invention is incorporated into the chromosome of the transformed host cell by homologous recombination. As this region, a portion of the chromosome of the host cell can be arbitrarily utilized. Otherwise, an auxotrophic complementary gene, or a promoter, a terminator or the like in the expression cassette can also be utilized.

The auxotrophic complementary gene in the present invention is not particularly limited, as long as it is a gene that complements the amino acid or nucleic acid auxotrophy of the host cell. Specific examples of such an auxotrophic complementary gene include a URA3 gene, a LEU2 gene, an ADE1 gene, and a HIS4 gene. In each of uracil, leucine, adenine and histidine auxotrophic strains, these genes can be selected by the recovery of the phenotypes of prototrophic strains.

The selection marker gene according in the present invention, such as a drug resistance gene, is not particularly limited, as long as it is a gene that imparts to a host cell, drug resistance that is not possessed by the host cell. Specific examples of such a selection marker gene include a G418 resistance gene, a zeocin resistance gene, and a hygromycin resistance gene. These genes can be selected based on resistance on a medium containing G418, zeocin and hygromycin, respectively. The auxotrophic selection marker used upon production of a yeast host cannot be used herein, if the selection marker is not destroyed. In this case, the selection marker may be recovered, and a method known to a person skilled in the art can be applied herein.

The autonomously replicating sequence in the present invention means a sequence that acts as a replication origin for the recombinant vector of the present invention in a host cell and enables autonomous replication.

The recombinant vector of the present invention means a recombinant vector comprising the Fd chain gene or L chain gene of the present invention described in the present description. The recombinant vector preferably comprises both the Fd chain gene and the L chain gene. Specific examples of the recombinant vector of the present invention include:
(a) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene of an antibody;
(b) a recombinant vector, which comprises an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody, and a Fd chain gene of an antibody; and
(c) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody.

Preferred examples of the alignment of individual constituents comprised in the recombinant vector of the present invention from the 5'-terminal side to the 3'-terminal side are as follows:
(1) first promoter sequence-first signal sequence-L chain gene-second promoter sequence-second signal sequence-Fd chain gene-terminator sequence;
(2) first promoter sequence-first signal sequence-Fd chain gene-second promoter sequence-second signal sequence-L chain gene-terminator sequence; and
(3) a combination of an expression vector comprising (first promoter sequence-first signal sequence-L chain gene-first terminator sequence), with an expression vector comprising (second promoter sequence-second signal sequence-Fd chain gene-second terminator sequence).

In (1) to (3) above, the first promoter may be identical to or different from the second promoter. The first and second promoters are preferably MOX promoters or GAP promoters of *Hansenula polymorpha* (preferably, *Hansenula polymorpha* as a host).

In (1) to (3) above, the first signal sequence may be identical to or different from the second signal sequence. The first and second signal sequences are preferably Mating Factor α (MFα) prepro signals of *Saccharomyces cerevisiae*.

In (3) above, the first terminator sequence may be identical to or different from the second terminator sequence. The first and second terminator sequences are preferably the terminator sequences of the MOX gene of *Hansenula polymorpha*.

The host in the present invention is not particularly limited, as long as the recombinant vector comprising the Fd chain gene and/or L chain gene of the present invention can be introduced therein and as a result, the host can produce a Fab-type antibody. Preferred examples of such a host include yeast, molds, animal cells, transgenic animals, *Escherichia coli*, and a cell-free protein synthesis system. Among these, yeast is preferable, methanol-assimilating yeast is more preferable, and methanol-assimilating yeast belonging to the genus *Ogataea* or the genus *Komagataella* is even more preferable. Among the methanol-assimilating yeast species belonging to the genus *Ogataea*, *Ogataea polymorpha* and *Ogataea minuta* are preferable, and among the methanol-assimilating yeast species belonging to genus *Komagataella*, *Komagataella pastoris* is preferable.

The transformant in the present invention means a host, into which the recombinant vector of the present invention has been introduced. The transformant of the present invention can be selectively obtained using, as an indicator, a phenotype obtained with an auxotrophic complementary gene or a drug resistance gene comprised in a recombinant vector.

As a method for producing the Fab-type antibody of the present invention, the Fab-type antibody is obtained by culturing the above-described transformant and then recovering the produced Fab-type antibody. An example of the production method is a secretion method comprising culturing the above-described transformant and then accumulating the produced Fab-type antibody in the culture supernatant thereof.

The term "secretory production" is used in the present invention to mean that a transformant is subjected to liquid culture and a Fab-type antibody is then allowed to accumulate not only in a cell mass, but also in a culture supernatant. Such secretory production is carried out by allowing the Fd chain and/or L chain of a Fab-type antibody to express as a protein fused with a secretory signal. Fusion with a secretory signal can be carried out, for example, by introducing a nucleotide sequence encoding a signal sequence into the 5'-terminus of a nucleotide sequence encoding the Fd chain and/or L chain of a Fab-type antibody.

The nucleotide sequence encoding a signal sequence according to the present invention is not particularly limited, as long as it encodes a signal sequence that may allow a host cell to secrete and express the Fab-type antibody. Examples of such a nucleotide sequence include nucleotide sequences encoding the signal sequences of the Mating Factor α (MFα) of *Saccharomyces cerevisiae*, acid phosphatase (PHO1) of *Ogataea polymorpha* or *Komagataella pastoris*, invertase (SUC2) of *Saccharomyces cerevisiae*, PLB1 of *Saccharomyces cerevisiae*, bovine serum albumin (BSA), human serum albumin (HSA), and immunoglobulin.

The medium used for the transformant according to the present invention is not particularly limited, and any type of medium can be used, as long as it is a medium containing a nutrient source generally assimilated by host cells. Examples of the nutrient source that can be used herein include sugars such as glucose, sucrose or maltose, organic acids such as lactic acid, acetic acid, citric acid or propionic acid, alcohols such as methanol, ethanol or glycerol, hydrocarbons such as paraffin, oils and fats such as soybean oil or rapeseed oil, carbon sources such as a mixture of the aforementioned substances, nitrogen sources such as ammonium sulfate, ammonium phosphate, urea, yeast extract, meat extract, peptone or corn steep liquor, other nutrient sources such as inorganic salts or vitamins. A common medium prepared by appropriately mixing and/or blending these substances can be used herein. It is particularly preferable to use glycerol or methanol as a carbon source. Moreover, as a culture method, any one of batch culture, continuous culture and domed culture can be applied.

In general, the culture can be carried out under ordinary conditions, and for example, the culture can be carried out by aerobically culturing cells at pH 2.5 to 10.0 in a temperature range of 10° C. to 48° C. for 10 hours to 10 days.

With regard to the transformant of the present invention, when the transformant is cultured to produce a Fab-type antibody, the secretory production amount of the Fab-type antibody in the obtained culture supernatant is preferably 2.0 mg/L or more (more preferably, 2.5 mg/L or more). The transformant, regarding which, when the transformant is cultured to produce a Fab-type antibody, the secretory production amount of the Fab-type antibody in the obtained culture supernatant is preferably 2.0 mg/L or more (more preferably, 2.5 mg/L or more), means a transformant, regarding which, the concentration of a Fab-type antibody is 2.0 mg/L or more (or 2.5 mg/L or more), when an expression vector comprising the Fab-type antibody gene described in Example 1 is used, yeast is transformed with the expression vector by the method described in Example 2, the obtained transformant is then cultured by the methods described in Examples 3 and 4, and the secretory production amount of the Fab-type antibody in the thus obtained culture supernatant is then analyzed.

In the case of secretory production, the method of recovering the Fab-type antibody of the present invention comprises a step of preparing a culture supernatant from a culture solution by centrifugation or the like, or a step of isolating a Fab-type antibody from the culture supernatant and purifying it by any given method. The Fab-type antibody can be isolated and purified from the culture supernatant by appropriately combining known protein purification methods with one another and using the thus combined methods. For instance, a transformant is cultured in a suitable medium, a cell mass is then removed from the culture supernatant by centrifugation of the culture solution or by a filtration treatment, and the thus obtained culture supernatant is subjected to a method such as salting-out (ammonium sulfate precipitation, sodium phosphate precipitation, etc.), solvent precipitation (a protein fraction precipitation method using acetone, ethanol or the like), dialysis, gel filtration chromatography, ion exchange chromatography, hydrophobic chromatography, affinity chromatography, reverse phase chromatography or ultrafiltration, so that a Fab-type antibody can be recovered from the culture supernatant. The thus recovered Fab-type antibody can be directly used. However, the recovered Fab-type antibody can also be used, after a modification for causing a pharmacological change such as PEGylation, or a modification for adding the functions of enzyme, isotope or the like, has been added to the antibody. In addition, various types of formulation treatments may also be used.

Antibody-Drug Conjugate

A non-limiting example of the Fab-type antibody of the present invention preferably includes an antibody-drug conjugate wherein a drug having cytotoxicity is conjugated to the Fab-type antibody or a fragment thereof. An antibody-drug conjugate may be hereinafter referred to as ADC. Specifically, the antibody-drug conjugate used in the present invention is obtained by using a growth inhibitor or a cytotoxic substance such as toxic peptide or radioactive substance.

The radioactive substance in the present invention refers to a substance comprising radioisotope. The radioisotope is not particularly limited, and any radioisotope can be used. For example, $^{32}P$, $^{14}C$, $^{125}I$, $^{3}H$, $^{131}I$, $^{186}Re$, $^{188}Re$ and the like can be used. Such antibody-drug conjugate can be obtained by chemically modifying the obtained antibody. A growth inhibitor or a cytotoxic substance is conjugated to an antibody via chemical bond by a linker molecule in such a manner that the growth inhibitor or the cytotoxic substance and the antibody can be chemically conjugated (for example, can be covalently bound) with each other.

Preferably, the binding agent (linker) is a cleavable linker. More preferably, the linker is cleaved under a moderate condition (namely, an intracellular condition such that the drug activity is not affected). The examples of suitable cleavable linkers include a disulfide linker, acid-unstable linker, photo-unstable linker, peptidase-unstable linker, and esterase-unstable linker. A linker comprising a disulfide is a linker which can be cleaved via disulfide exchange which may occur under physiological condition. The acid-unstable linker is linker which can be cleaved by acidic pH. For example, certain intracellular compartment such as endosome or lysosome has acidic pH (4 to 5), and provides a condition suitable for cleavage of acid-unstable linker. The photo-unstable linker is useful in body surface and many body cavities which can be exposed to light. Further, tissue can transmit infrared light. The peptidase-unstable linker can be used for cleaving certain intracellular and extracellular peptides.

These ADCs can be obtained as a molecular type such as bispecific antibody which is designed using gene recombinant technology in such a manner that the antibody can recognize a growth inhibitor or a cytotoxic substance such as toxic peptide or radioactive substance, in addition to the aforementioned chemical modification. The "Fab-type antibody" in the present invention includes these antibodies.

A non-limiting example of the antibody-drug conjugate according to the present invention includes an antibody which was modified with a toxic peptide such as ricin, abrin, ribonuclease, Onconase, DNase I, *Staphylococcus* enterotoxin A, poke weed anti-virus protein, gelonin, diphtheria toxin, *Pseudomonas* exotoxin, *Pseudomonas* endotoxin, L-asparaginase and PEG L-asparaginase. In another embodiment, a combination of one or more growth inhibitors and a cytotoxic substance such as toxic peptide can be used for modification of an antibody. As mentioned above, covalent bonding or non-covalent bonding can be used for conjugation of an antibody and the growth inhibitor or the cytotoxic substance such as toxic peptide or radioactive substance. The method for production of ADC obtained by conjugation of the growth inhibitor or the cytotoxic substance such as toxic peptide or radioactive substance is known. For example, the linking group in a case where an antibody is directly bound to a growth inhibitor or a cytotoxic substance such as toxic peptide or radioactive substance, is disulfide bond where SH group is used for bonding. Specifically, an antibody wherein an intramolecular disulfide bond of the Fc region is reduced by a reducing agent such as dithiothreitol, and a growth inhibitor or cytotoxic substance where an intramolecular disulfide bond is reduced, are conjugated via disulfide bond. Before conjugation, any one of the antibody and the growth inhibitor or cytotoxic substance may be activated with activation promoting agent such as Ellman's reagent, so that the formation of disulfide bond can be promoted. Other methods of directly binding an antibody to a growth inhibitor or a cytotoxic substance such as toxic peptide or radioactive substance include, for example, a method of using Schiff's base, a carbodiimide method, an active ester method (N-hydroxysuccinimide method), a method using mixed anhydride, and a method using diazo reaction, as non-limiting preferred examples.

The toxic peptide used in the present invention can be exemplified as mentioned below.

Diphtheria toxin A Chain (Oeltmann et al., Methods in Enzymology, (1988), 165, 204-210)

*Pseudomonas* Exotoxin (Pai et al. Nat. Med. (1996)2 (3), 350-353)

Ricin A Chain (Fulton et al. J. Biol. Chem. (1986) 261, 5314-5319, Sivam et al. Cancer Res. (1987) 47, 3169-3173, Cumber et al. J. Immunol. Methods (1990) 135, 15-24, Wawrzynczak et al. Cancer Res. (1990) 50, 7519-7562, and Gheeite et al. J. Immunol. Methods (1991) 142, 223-230)

Deglicosylated Ricin A Chain (Thorpe et al. Cancer Res. (1987)47, 5924-5931)

Abrin A Chain (Wawrzynczak et al. Br. J. Cancer (1992) 66, 361-366), Wawrzynczak et al. Cancer Res (1990) 50, 7519-7562, Sivam et al. Cancer Res. (1987) 47, 3169-3173), and Thorpe et al. Cancer Res. (1987) 47, 5924-5931)

Gelonin (Sivam et al. Cancer Res. (1987) 47, 3169-3173, Cumber et al. J. Immunol. Methods (1990) 135, 15-24, Wawrzynczak et al. Cancer Res. (1990) 50, 7519-7562, and Bolognesi et al. Clin. Exp. Immunol. (1992) 89, 341-346)

PAP-s or Pokeweed anti-viral protein fromseeds (Bolognesi et al. Clin. Exp. Immunol. (1992), 89, 341-346)

Briodin (Bolognesi et al. Clin. Exp. Immunol. (1992) 89, 341-346)

Saporin (Bolognesi et al, Clin. Exp. Immunol. (1992), 89, 341-346)

Momordin (Cumber et al, J. Immunol. Methods (1990) 135, 15-24; Wawrzynczak et al, Cancer Res. (1990) 50, 7519-7562; and Bolognesi et al, Clin. Exp. Immunol. (1992) 89, 341-346)

Momorcochin (Bolognesi et al. Clin. Exp. Immunol. (1992) 89, 341-346)

Dianthin 32 (Bolognesi et al. Clin. Exp. Immunol. (1992) 89, 341-346)

Dianthin 30 (Stirpe et al. FEBS Let. (1986) 195, 1-8)

Modeccin (Stirpe et al. FEBS Let. (1986) 195, 1-8)

Viscumin (Stirpe et al. FEBS Let. (1986) 195, 1-8)

Volkesin (Stirpe et al. FEBS Let. (1986) 195, 1-8)

Dodecandrin (Stirpe et al. FEBS Let. (1986) 195, 1-8)

Tritin (Stirpe et al. FEBS Let. (1986) 195, 1-8)

Luffin (Stirpe et al. FEBS Let. (1986) 195, 1-8)

Trichokirin (Casellas et al. Eur. J. Biochem. (1988) 176, 581-588), and Bolognesi et al. Clin. Exp. Immunol. (1992) 89, 341-346)

Drugs or toxins of protein or peptide can be conjugated to an antibody by genetic engineering method. Specifically, a recombinant vector can be constructed by incorporating, into an expression vector, a recombinant DNA wherein DNA which encodes the aforementioned toxic peptide and DNA which encodes the antibody of the present invention are fused in frame. The vector is introduced into a suitable host cell to obtain a transformant cell. The transformant cell is cultured so as to allow the incorporated DNA to be expressed in the cells. An antibody-drug conjugate with toxic peptide can be obtained by isolation and purification from the culture solution. When a protein fused with an antibody is obtained, these DNAs are often ligated in such a manner that proteinous drug or toxin is arranged at the C-terminal of an antibody, but the present invention is not limited to this embodiment. A peptide linker may be present between the antibody and the proteinous drug or toxin.

Imaging Antibody

Preparation and use of antibody preparation for use in diagnosis in vivo are well-known in the art. For example, a conjugate of indium-111 labeled antibody and a chelating agent (antibody-chelating agent) is used in imaging of tumors which expresses carcinoembryonic antigen by radioimmunoscintigraphy. Especially, this antibody-chelating agent is used for detection of tumor in a patient suspected of having recurrent colorectal cancer. An antibody having a paramagnetic ion as a label used in magnetic resonance imaging is also known.

The Fab-type antibody of the present invention can be injected, for example, to a patient suspected of having a cancer for the purpose of diagnosis of disease state of the patient, diagnosis of disease stage or the like. A label to be used can be selected depending on the imaging mode to be used. For example, radioactive label such as indium-111 (111In), technetium-99m (99mTc) or Iodine-131 (131I) can be used for flat scan or single photon laminography. A positron-emission label such as fluorine-18 (18F) can be used for positron tomography. A paramagnetic ion such as gadolinium (III) or manganese (II) can be used for magnetic resonance imaging. Seeding of cancer can be judged by examining the localization of label. The presence or absence of cancer in organ or tissue can be determined by the amount of label in the organ or the tissue.

Therefore, preferably, the antibody in a diagnostic agent or a therapeutic agent is chemically bound to or is bound to by genetic engineering method, radioisotope element, therapeutic protein, small molecule drug, a virus vector having therapeutic gene or the like.

Pegylation

The Fab-type antibody of the present invention may be modified by binding polyethylene glycol (PEG) thereto via cysteine which was ligated to the C-terminal of the antibody or cysteine in the amino acid sequence which was ligated to the C-terminal of the antibody. The binding of PEG to the antibody can be carried out by a method known in the art. In the present invention, any PEG or its derivative of straight chain or branched chain having any average molecular weight can be used, and the PEG or its derivative can be easily selected by a skilled person in the art depending on purpose of use. For example, vascular permeability is remarkably increased in tumor tissues or inflammatory reactions as compared in normal tissues, and a substance which reached leaks out blood vessel and tends to accumulate in tumors or inflammatory tissues (EPR effect). It is also known that a substance of small molecular weight tends to be resorbed into blood vessel and a substance of large molecular weight tends not to be resorbed into blood vessel. Therefore, PEG of high average molecular weight (for example, about 40,000 Da) may be bound in order to enhance retention of antibody in disease tissue. PEG of small average molecular weight (for example, about 10,000 Da) may be bound when rapid body's excretion is desired. In order to facilitate the binding of PRG to cysteine which was ligated to the C-terminal of the antibody or cysteine in the amino acid sequence which was ligated to the C-terminal of the antibody, a derivative of PEG may be used. The average molecular weight of PEG is generally about 500 Da to about 50,000 Da, preferably about 5,000 Da to about 40,000 Da, and more preferably about 10,000 Da to about 40,000 Da.

EXAMPLES

The present invention will be more specifically described in the following examples. However, these examples are not intended to limit the scope of the present invention. It is to be noted that detailed operation methods regarding the recombination DNA techniques used in the following Examples are described in the following publications: Molecular Cloning 2nd Edition (Cold Spring Harbor Laboratory Press, 1989), Current Protocols in Molecular Biology (Greene Publishing Associates and Wiley-Interscience), and Current Protocols in Molecular Biology (Greene Publishing Associates and Wiley-Interscience).

Moreover, the plasmids obtained in the following Examples have been amplified, using the transformant that had been obtained by treating *Escherichia coli* DH5α competent cells (manufactured by TAKARA BIO INC.) under the conditions described in the instruction manual included therewith.

Using Prime STAR HS DNA Polymerase (manufactured by TAKARA BIO INC.), PCR was carried out under the reaction conditions described in the manual included therewith.

(Example 1) Construction of pUC-LEU2-PmMfTm

A MOX promoter (SEQ ID NO: 18), a MOX terminator (SEQ ID NO: 19), and a LEU2 gene (SEQ ID NO: 20), which were to be used in construction of an expression vector for expression of an antibody, were prepared by PCR using the genomic DNA of the *Hansenula polymorpha* 8V strain as a template. A Mating Factor α prepro signal (MFα, SEQ ID NO: 21) was prepared by PCR using the genomic DNA of the *Saccharomyces cerevisiae* S288c strain as a template. An antibody gene was prepared by PCR, using, as templates, an L chain (SEQ ID NO: 22) and an H chain (SEQ ID NO: 23) that had been chemically synthesized based on the published sequence information of a completely humanized anti-TNF-α antibody (adalimumab; HUMIRA (registered trademark)) (Japanese Patent Laid-Open No. 2009-082033 A).

A gene fragment (SEQ ID NO: 24) having the site HindIII-NotI-BamHI-SpeI-BglII-XbaI-EcoRI was totally synthesized, and this gene fragment was then inserted into the HindIII-EcoRI site of pUC19 to prepare pUC-1. A gene fragment having HindIII sites at both ends of a LEU2 gene was prepared by PCR using primers 1 and 2 (SEQ ID NOS: 25 and 26), and after completion of the HindIII treatment, the gene fragment was inserted into the HindIII site of pUC-1 (pUC-LEU2). Subsequently, a gene fragment having BmHI sites at both ends of a MOX promoter was prepared by PCR using primers 3 and 4 (SEQ ID NOS: 27 and 28), and after completion of the BamHI treatment, the gene fragment was inserted into the BamHI site of pUC-LEU2 (pUC-LEU2-Pm). A gene fragment having SpeI site at the 5'-terminal side of MFα and having BglII site at the 3'-terminal side thereof was prepared by PCR using primers 5 and 6 (SEQ ID NOS: 29 and 30), and after completion of the SpeI and BglII treatments, the gene fragment was inserted into the SpeI-BglII site of pUC-LEU2-Pm (pUC-LEU2-PmMf). A gene fragment having XbaI sites at both ends of a MOX terminator was prepared by PCR using primers 7 and 8 (SEQ ID NOS: 31 and 32), and after completion of the XbaI treatment, the gene fragment was inserted into the XbaI site of pUC-LEU2-PmMf (pUC-LEU2-PmMfTm).

(Comparative Example 1) Construction of Recombinant Vector Expressing Fab-Type Antibody A gene fragment having BglII sites at both ends of an L chain was prepared by PCR using primers 9 and 10 (SEQ ID NOS: 33 and 34). This gene fragment was treated with BglII, and was then inserted into the BglII site of pUC-LEU2-PmMfTm to construct pUC-LEU2-PmMfLTm. A gene fragment having BglII sites at both ends of an Fd chain was prepared by PCR using primers 11 and 12 (SEQ ID NOS: 35 and 36). This gene fragment was treated with BglII, and was then inserted into the BglII site of pUC-LEU2-PmMfTm to construct pUC-LEU2-PmMfFTm. Using the pUC-LEU2-PmMfLTm as a template, a gene fragment having EcoRI sites at both ends of a gene fragment, to which a MOX promoter, MFα, an L chain, and some of a MOX terminator were ligated, was prepared by PCR using primers 13 and 14 (SEQ ID NOS: 37 and 38). This gene fragment was treated with EcoRI, and was then inserted into the EcoRI site of pUC-LEU2-PmMfFTm, so as to construct pUC-LEU2-Pm- MfFTm-PmMfLtm. This expression vector is designed such that the L chain and Fd chain of a Fab-type antibody are each allowed to express under the control of different MOX promoters.

(Comparative Example 2) Obtainment of Transformant

The Fab-type antibody expression vector constructed in Comparative Example 1 was cleaved with the EcoRV site in the MOX terminator, so as to linearize it. This fragment was subject to the method described in Example 3, so as to transform *Ogataea polymorpha*.

(Comparative Example 3) Culture of Transformant and Preparation of Culture Supernatant A culture supernatant of the Fab-type antibody expression vector-introduced strain obtained in Comparative Example 2 was prepared in the same manner as the method described in Example 4.

(Comparative Example 4) Quantification of Fab-Type Antibody

The secretory production amount of a Fab-type antibody in the culture supernatant obtained in Comparative Example 3 was analyzed by a sandwich ELISA (Enzyme-Linked Immunosorbent Assay) method, as with Example 5.

The Fd chain genes (SEQ ID NOS: 5 to 9) of the present invention were each prepared by PCR using the above described pUC-LEU2-PmMfFTm as a template.

(Example 2) Construction of Individual Recombinant Vectors Each Expressing Fab-Type Antibody A fragment wherein a nucleotide sequences encoding an Fd chain, a nucleotide sequence encoding any one of the amino acid sequences Asp, Asp-Lys, Asp-Lys-Thr, Asp-Lys-Thr-His (SEQ ID NO: 1) and Asp-Lys-Thr-His-Thr (SEQ ID NO: 2), and a nucleotide sequence encoding a termination codon were fused, was prepared by PCR.

An Fd chain gene fragment with which a nucleotide sequence encoding Asp was fused, was obtained by PCR using primer 15 (SEQ ID NO: 10) and primer 16 (SEQ ID NO: 11); an Fd chain gene fragment, with which a nucleotide sequence encoding Asp-Lys was fused, was obtained by PCR using primer 15 and primer 17 (SEQ ID NO: 12); an Fd chain gene fragment, with which a nucleotide sequence encoding Asp-Lys-Thr was fused, was obtained by PCR using primer 1 and primer 18 (SEQ ID NO: 13); an Fd chain gene fragment, with which a nucleotide sequence encoding Asp-Lys-Thr-His (SEQ ID NO: 1) was fused, was obtained by PCR using primer 15 and primer 19 (SEQ ID NO: 14); and an Fd chain gene fragment, with which a nucleotide sequence encoding Asp-Lys-Thr-His-Thr (SEQ ID NO: 2) was fused, was obtained by PCR using primer 15 and primer 20 (SEQ ID NO: 15). The obtained gene fragments were each treated with BglII, and the treated gene fragments were each inserted into the BglII site of the pUC-LEU2-PmMfTm described in Example 1, so as to construct plasmids each comprising an Fd chain gene containing a nucleotide sequence encoding any one of Asp, Asp-Lys, Asp-Lys-Thr, Asp-Lys-Thr-His (SEQ ID NO: 1) and Asp-Lys-Thr-His-Thr (SEQ ID NO: 2). Using pUC-LEU2-PmMfLTm as a template, a gene fragment having EcoRI sites at both ends of a gene fragment, to which a MOX promoter, MFα, an L chain, and some of a MOX terminator were ligated, was prepared by PCR using primers 13 and 14 (SEQ ID NOS: 37 and 38). This gene fragment was treated with EcoRI, and was then inserted into the EcoRI site of each plasmid comprising an Fd chain gene containing a nucleotide sequence encoding any one of the aforementioned Asp, Asp-Lys, Asp-Lys-Thr, Asp-Lys-Thr-His (SEQ ID NO: 1) and Asp-Lys-Thr-His-Thr (SEQ ID NO: 2), so as to construct Fab-type antibody expression vectors each comprising an Fd chain gene containing a nucleotide sequence encoding any one of Asp, Asp-Lys, Asp-Lys-Thr, Asp-Lys-Thr-His (SEQ ID NO: 1) and Asp-Lys-Thr-His-Thr (SEQ ID NO: 2).

(Example 3) Obtainment of Transformant

Various types of recombinant vectors each expressing a Fab-type antibody constructed in Example 2 were cleaved with the EcoRV site in the MOX terminator, so as to linearize them. Using these fragments, *Ogataea polymorpha* was transformed. Specifically, *Ogataea polymorpha* BY4329 (derived from NCYC495, leu1-1) was inoculated into 3 ml of YPD medium (1% yeast extract bacto (Difco), 2% tryptone bacto (manufactured by Difco), and 2% glucose), and the obtained mixture was then subjected to a shaking culture at 37° C. overnight to obtain a preculture solution. 500 μl of the obtained preculture solution was inoculated into 50 ml of YPD medium, and the obtained mixture was then subjected to a shaking culture at 30° C., so as to result in OD600 of 1 to 1.5. Thereafter, cells were harvested (3000×g, 10 min, 20° C.). The cell mass was suspended in 10 ml of 50 mM potassium phosphate buffer (containing 25 mM DTT, pH 7.5), and the suspension was then incubated at 37° C. for 15 minutes. After the harvest of the cells (3000×g, 10 min, 4° C.), the cell mass was re-suspended in 50 ml of ice-cooled STM buffer (270 mM sucrose, 10 mM Tris-HCl, 1 mM magnesium chloride, pH 7.5). After the harvest of the cells (3000×g, 10 min, 4° C.), the cell mass was re-suspended in 25 ml of the ice-cooled STM buffer. After the harvest of the cells (3000×g, 10 min, 4° C.), the cell mass was suspended in 250 μl of the ice-cooled STM buffer, and this solution was used as a competent cell solution. 60 μl of this competent cell solution was mixed with 3 μl of each linear plasmids solution (the amount of DNA: 0.5 to 1 μg), and the obtained mixture was then transferred into a cuvette for electroporation (disposable cuvette electrodes; distance between electrodes: 2 mm; manufactured by BM Equipment Co., Ltd.), followed by performing electroporation under conditions of 7.5 kV/cm, 10 μF, and 900Ω. Thereafter, the cell mass was suspended in 1 ml of YPD medium, and the suspension was then left at rest at 37° C. for 1 hour. The cells were harvested (3000×g, 5 min, room temperature), the cell mass was then washed with 1 ml of normal saline, and the cells were harvested again (3000×g, 5 min, room temperature). The cell mass was suspended in an appropriate amount of normal saline, and the suspension was then applied onto an SD medium agar plate (0.67% yeast nitrogen base (manufactured by Difco), 1% glucose). Strains growing in a static culture at 30° C. for 3 days were selected, and various types of Fab-type antibody expressing strains were obtained.

(Example 4) Culture of Transformant and Preparation of Culture Supernatant

A culture supernatant was prepared as follows. Specifically, various types of Fab-type antibody expressing strains obtained in Example 3 were each inoculated in 2 ml of BMGMY medium (1% yeast extract bacto, 2% peptone, 1.34% yeast nitrogen base, 0.4 mg/l biotin, 100 mM potassium phosphate (pH 6.0), 1% glycerol, and 1% methanol), the obtained mixture was then subjected to a shaking culture at 30° C. for 72 hours, and the obtained culture was then centrifuged (15,000 rpm, 1 min, 4° C.) to prepare a culture supernatant.

(Example 5) Quantification of Fab-Type Antibody

The secretory production amount of a Fab-type antibody in the culture supernatant was analyzed by a sandwich ELISA (Enzyme-Linked Immunosorbent Assay).

For the sandwich ELISA, Anti IgG (Fd), Human (Sheep) (manufactured by The Binding Site Group) that had been 2,500 times diluted with a fixing buffer (0.1M sodium carbonate buffer, pH 9.6) was added in an amount of 50 μl/well to an ELISA plate (MaxiSorp; manufactured by NUNC), and it was then incubated at 4° C. overnight. After completion of the incubation, the solution in the well was discarded, and 5-fold diluted Immunoblock (manufactured by Dainippon Pharma Co., Ltd.) was then added in an amount of 250 μl/well to the well. It was left at rest at room temperature for 1 hour, so that it was blocked. Each well was washed with PBST (PBS (manufactured by TAKARA BIO INC.)+0.1% Tween 20) three times, and a serially diluted standard Fab-type antibody (Anti-Human IgGFab; manufactured by Rockland) and a diluted solution of the culture supernatant were added in an amount of 50 μl/well to the well. Thereafter, the reaction was carried out at room temperature for 1 hour. The solution in the well was discarded, and the well was then washed with PBST twice. After that, Anti-Human IgG (Fab SPECIFIC) PEROXIDASE CONJUGATE Antibody developed in Goat Affinity Isolated Antibody (manufactured by SIGMA), which had been 8,000 times diluted with PBSTIB (PBST+2% Immunoblock) solution, was added in an amount of 50 μl/well to the well, and it was then reacted at room temperature for 1 hour. Thereafter, the solution in the well was discarded, and the well was then washed with PBST four times. TMB 1-Component Microwell Peroxidase Substrate, SureBlue (manufactured by KPL) was added in an amount of 100 μl/well to the well, and it was then left at rest at room temperature for 20 minutes. Thereafter, TMB Stop Solution (manufactured by KPL) was added in an amount of 100 μl/well to the well to terminate the reaction, and the absorbance at 450 nm was then measured using Microplate Reader (BenchMark Plus; manufactured by Bio-Rad). The Fab-type antibody in the culture supernatant was quantified using a calibration curve of standard protein. The results are shown in Table 1. As shown in Table 1, it became clear that the production amount of the Fab-type antibody that was fused with any one of Asp, Asp-Lys, Asp-Lys-Thr, Asp-Lys-Thr-His (SEQ ID NO: 1) and Asp-Lys-Thr-His-Thr (SEQ ID NO: 2) was approximately 5 times higher than that of an unfused Fab-type antibody.

TABLE 1

| fusion peptide | TOD600 | Fab (mg/L) |
| --- | --- | --- |
| none (control) | 40.5 | 0.55 |
| Asp | 39.7 | 2.83 |
| Asp-Lys | 40.8 | 2.77 |
| Asp-Lys-Thr (SEQ ID NO: 1) | 40.8 | 2.90 |

TABLE 1-continued

| fusion peptide | TOD600 | Fab (mg/L) |
| --- | --- | --- |
| Asp-Lys-Thr-His (SEQ ID NO: 2) | 40.5 | 2.70 |
| Asp-Lys-Thr-His-Thr | 41.7 | 2.67 |

(Example 6) Construction 2 of Various Fab-Type Antibody Expression Vectors

A fragment, with which a nucleotide sequence encoding an Fd chain, a nucleotide sequence encoding any one of the amino acids Gly, Ala, Val, Leu, Ile, Cys, Met, Ser, Thr, Tyr, Phe, Trp, Pro, Glu, Asn, Gln, Lys, Arg and His, and a nucleotide sequence encoding a termination codon were fused, was prepared by PCR.

An Fd chain gene fragment, with which a nucleotide sequence encoding Gly was fused, was prepared by PCR using primer 15 and primer 21 (SEQ ID NO: 39); an Fd chain gene fragment, with which a nucleotide sequence encoding Ala was fused, was prepared by PCR using primer 15 and primer 22 (SEQ ID NO: 40); an Fd chain gene fragment, with which a nucleotide sequence encoding Val was fused, was prepared by PCR using primer 15 and primer 23 (SEQ ID NO: 41); an Fd chain gene fragment, with which a nucleotide sequence encoding Leu was fused, was prepared by PCR using primer 15 and primer 24 (SEQ ID NO: 42); an Fd chain gene fragment, with which a nucleotide sequence encoding Ile was fused, was prepared by PCR using primer 15 and primer 25 (SEQ ID NO: 43); an Fd chain gene fragment, with which a nucleotide sequence encoding Cys was fused, was prepared by PCR using primer 15 and primer 26 (SEQ ID NO: 44); an Fd chain gene fragment, with which a nucleotide sequence encoding Met was fused, was prepared by PCR using primer 15 and primer 27 (SEQ ID NO: 45); an Fd chain gene fragment, with which a nucleotide sequence encoding Ser was fused, was prepared by PCR using primer 15 and primer 28 (SEQ ID NO: 46); an Fd chain gene fragment, with which a nucleotide sequence encoding Thr was fused, was prepared by PCR using primer 15 and primer 29 (SEQ ID NO: 47); an Fd chain gene fragment, with which a nucleotide sequence encoding Tyr was fused, was prepared by PCR using primer 15 and primer 30 (SEQ ID NO: 48); an Fd chain gene fragment, with which a nucleotide sequence encoding Phe was fused, was prepared by PCR using primer 15 and primer 31 (SEQ ID NO: 49); an Fd chain gene fragment, with which a nucleotide sequence encoding Trp was fused, was prepared by PCR using primer 15 and primer 32 (SEQ ID NO: 50); an Fd chain gene fragment, with which a nucleotide sequence encoding Pro was fused, was prepared by PCR using primer 15 and primer 33 (SEQ ID NO: 51); an Fd chain gene fragment, with which a nucleotide sequence encoding Glu was fused, was prepared by PCR using primer 15 and primer 34 (SEQ ID NO: 52); an Fd chain gene fragment, with which a nucleotide sequence encoding Asn was fused, was prepared by PCR using primer 15 and primer 35 (SEQ ID NO: 53); an Fd chain gene fragment, with which a nucleotide sequence encoding Gln was fused, was prepared by PCR using primer 15 and primer 36 (SEQ ID NO: 54); an Fd chain gene fragment, with which a nucleotide sequence encoding Lys was fused, was prepared by PCR using primer 15 and primer 37 (SEQ ID NO: 55); an Fd chain gene fragment, with which a nucleotide sequence encoding Arg was fused, was prepared by PCR using primer 15 and primer 38 (SEQ ID NO: 56); and an Fd chain gene fragment, with which a nucleotide sequence encoding His was fused, was prepared by PCR using primer 15 and primer 39 (SEQ ID NO: 57). The obtained fragments were each treated with BglII, and thereafter, they were each inserted into the BglII site of the pUC-LEU2-PmMfTm described in Example 1, so as to construct plasmids each comprising an Fd chain gene containing a nucleotide sequence encoding any one of Gly, Ala, Val, Leu, Ile, Cys, Met, Ser, Thr, Tyr, Phe, Trp, Pro, Glu, Asn, Gln, Lys, Arg and His. Using pUC-LEU2-PmMfLTm as a template, a gene fragment having EcoRI sites at both ends of a gene fragment, to which a MOX promoter, MFα, an L chain, and some of a MOX terminator were ligated, was fused, was prepared by PCR using primers 13 and 14 (SEQ ID NOS: 37 and 38). This gene fragment was treated with EcoRI, and was then inserted into the EcoRI site of each plasmid comprising an Fd chain gene containing a nucleotide sequence encoding any one of the aforementioned Gly, Ala, Val, Leu, Ile, Cys, Met, Ser, Thr, Tyr, Phe, Trp, Pro, Glu, Asn, Gln, Lys, Arg and His, so as to construct Fab-type antibody expression vectors each comprising an Fd chain gene containing a nucleotide sequence encoding any one of Gly, Ala, Val, Leu, Ile, Cys, Met, Ser, Thr, Tyr, Phe, Trp, Pro, Glu, Asn, Gln, Lys, Arg and His.

(Example 7) Construction 3 of Various Fab-Type Antibody Expression Vectors

A fragment, with which a nucleotide sequence encoding an L chain, a nucleotide sequence encoding the amino acid Asp, and a nucleotide sequence encoding a termination codon were fused, was prepared by PCR.

An L chain gene fragment, with which a nucleotide sequence encoding Asp was fused, was obtained by performing PCR using primer 9 and primer 40 (SEQ ID NO: 58). This fragment was treated with BglII, and it was then inserted into the BglII site of the pUC-LEU2-PmMfTm described in Example 1, so as to construct a vector comprising the L chain gene containing the nucleotide sequence encoding Asp. Using this vector as a template, a gene fragment having EcoRI sites at both ends of a gene fragment, to which a MOX promoter, MFα, an L chain containing a nucleotide sequence encoding Asp, and some of a MOX terminator were ligated, was prepared by PCR using primers 13 and 14 (SEQ ID NOS: 37 and 38). This gene fragment was treated with EcoRI, and was then inserted into the EcoRI site of the pUC-LEU2-PmMfFTm described in Example 2, so as to construct various Fab-type antibody expression vectors comprising an L chain gene containing a nucleotide sequence encoding Asp.

(Example 8) Culture of Transformant and Preparation of Culture Supernatant

Various types of recombinant vectors each expressing a Fab-type antibody, which were constructed in Examples 6 and 7, were cleaved with the EcoRV site in the MOX terminator, so as to linearize them. These fragments were used to transform *Ogataea polymorpha* according to the method described in Example 2, so as to obtain various types of Fab-type antibody-expressing strains.

(Example 9) Culture of Transformant and Preparation of Culture Supernatant

Culture supernatants were prepared from various types of Fab-type antibody-expressing strains obtained in Example 8 in the same manner as that of Example 3.

(Example 10) Quantification of Fab-Type Antibody

The secretory production amount of a Fab-type antibody in the culture supernatant obtained in Example 9 was analyzed by the method described in Example 4.

The Fab-type antibody in the culture supernatant was quantified using a calibration curve of standard protein. The results are shown in Table 2. As shown in Table 2, it became clear that the production amount of the Fab-type antibody, with the Fd chain of which any one of Gly, Ala, Val, Leu, Ile, Cys, Met, Ser, Thr, Tyr, Phe, Trp, Pro, Glu, Asn, Gln, Lys, Arg and His was fused, and the production amount of the Fab-type antibody, with the L chain of which Asp is fused, are approximately 4 to 6 times higher than that of an unfused Fab-type antibody.

TABLE 2

| fusion amino acid | mononer | TOD600 | Fab (mg/L) |
|---|---|---|---|
| none (control) | — | 40.5 | 0.55 |
| Gly | Fd | 42.3 | 2.30 |
| Ala | Fd | 40.8 | 2.14 |
| Val | Fd | 41.8 | 2.03 |
| Leu | Fd | 41.1 | 2.18 |
| Ile | Fd | 40.9 | 2.22 |
| Cys | Fd | 41.6 | 2.09 |
| Met | Fd | 40.6 | 2.20 |
| Ser | Fd | 41.3 | 2.17 |
| Thr | Fd | 42.2 | 2.23 |
| Tyr | Fd | 40.4 | 2.47 |
| Phe | Fd | 41.6 | 2.86 |
| Trp | Fd | 42.3 | 3.19 |
| Pro | Fd | 42.0 | 2.44 |
| Glu | Fd | 40.6 | 2.35 |
| Asn | Fd | 40.9 | 2.48 |
| Gln | Fd | 40.9 | 2.45 |
| Lys | Fd | 40.4 | 2.49 |
| Arg | Fd | 40.4 | 2.49 |
| His | Fd | 40.2 | 2.60 |
| Asp | L | 41.5 | 2.83 |

(Comparative Example 5) Construction of Remicade-Derived Fab-Type Antibody Expression Vector A Remicade-derived Fab-type antibody gene was prepared by chemically synthesizing an L chain (SEQ ID NO: 59) and an Fd chain (SEQ ID NO: 60) based on the published sequence information of Remicade (Infliximab; Remicade (registered trademark)), and then performing PCR using the synthesized L and Fd chains as templates.

A gene fragment having BglII sites at both ends of a Remicade-derived L chain was prepared by PCR using primers 41 and 42 (SEQ ID NOS: 61 and 62). This gene fragment was treated with BglII, and was then inserted into the BglII site of the pUC-LEU2-PmMfTm described in Example 1 to construct pUC-LEU2-PmMfrLTm. A gene fragment having BglII sites at both ends of a Remicade-derived Fd chain was prepared by PCR using primers 43 and 44 (SEQ ID NOS: 63 and 64). This gene fragment was treated with BglII, and was then inserted into the BglII site of the pUC-LEU2-PmMfTm to construct pUC-LEU2-Pm- MfrFTm. Using pUC-LEU2-PmMfrLTm as a template, a gene fragment having EcoRI sites at both ends of a gene fragment, to which a MOX promoter, MFα, a Remicade-derived L chain, and some of a MOX terminator were ligated, was prepared by PCR using primers 13 and 14 (SEQ ID NOS: 37 and 38). This gene fragment was treated with EcoRI, and was then inserted into the EcoRI site of pUC-LEU2-PmMfrFTm, so as to construct pUC-LEU2-PmMfrFTm-PmMfrLtm. This expression vector is designed such that the L chain and Fd chain of a Remicade-derived Fab-type antibody are each allowed to express under the control of different MOX promoters.

(Comparative Example 6) Obtainment of Transformant

The Remicade-derived Fab-type antibody expression vector constructed in Comparative Example 5 was cleaved with the EcoRV site in the MOX terminator, so as to linearize it. This fragment was used to transform *Ogataea polymorpha* according to the method described in Example 3.

(Comparative Example 7) Culture of Transformant and Preparation of Culture Supernatant A culture supernatant of the Remicade-derived Fab-type antibody expression vector-introduced strain obtained in Comparative Example 6 was prepared in the same manner as the method described in Example 13.

(Comparative Example 8) Quantification of Fab-Type Antibody

The secretory production amount of a Fab-type antibody in the culture supernatant obtained in Comparative Example 7 was analyzed by a sandwich ELISA (Enzyme-Linked Immunosorbent Assay) method in the same manner as that of Example 5. The results are shown in Table 3.

(Example 11) Construction of Various Types of Remicade-Derived Fab-Type Antibody Expression Vectors A Remicade-derived Fd chain gene fragment, with which a nucleotide sequence encoding Asp was fused, was obtained by PCR using primer 43 and primer 45 (SEQ ID NO: 65). This gene fragment was treated with BglII, and was then inserted into the BglII site of the pUC-LEU2-PmMfTm described in Example 1, so as to construct a vector comprising a Remicade-derived Fd chain gene containing a nucleotide sequence encoding Asp. Using the pUC-LEU2-PmMfrLTm described in Comparative Example 2 as a template, a gene fragment having EcoRI sites at both ends of a gene fragment, to which a MOX promoter, MFα, a Remicade-derived L chain, and some of a MOX terminator were ligated, was prepared by PCR using primers 13 and 14 (SEQ ID NOS: 37 and 38). This gene fragment was treated with EcoRI, and was then inserted into the EcoRI site of the aforementioned vector comprising a Remicade-derived Fd chain gene containing a nucleotide sequence encoding Asp, so as to construct a recombinant vector expressing a Remicade-derived Fab-type antibody comprising a Remicade-derived Fd chain gene containing a nucleotide sequence encoding Asp.

(Example 12) Obtainment of Transformant

The recombinant vector expressing a Remicade-derived Fab-type antibody constructed in Example 11 was cleaved with the EcoRV site in the MOX terminator, so as to linearize it. This fragment was used to transform *Ogataea polymorpha* according to the method described in Example 2, so as to obtain a Remicade-derived Fab-type antibody-expressing strain.

(Example 13) Culture of Transformant and Preparation of Culture Supernatant

A culture supernatant was prepared as follows. That is to say, the Remicade-derived Fab-type antibody-expressing strain obtained in Example 12 was inoculated into 2 ml of BMGMY medium (1% yeast extract bacto, 2% peptone, 1.34% yeast nitrogen base, 0.4 mg/l biotin, 100 mM potassium phosphate (pH6.0), 1% glycerol, and 1% methanol), and the obtained mixture was then subjected to a shaking culture at 30° C. for 60 hours. Thereafter, 20 mg of methanol was added to the culture, and the obtained mixture was further subjected to a shaking culture at 30° C. for 24 hours. Thereafter, the culture was subjected to centrifugation (15,000 rpm, 1 min, 4° C.) to prepare a culture supernatant.

(Example 14) Quantification of Fab-Type Antibody

The secretory production amount of a Remicade-derived Fab-type antibody in the culture supernatant obtained in Example 13 was analyzed by the method described in Example 4.

The Remicade-derived Fab-type antibody in the culture supernatant was quantified using a calibration curve of standard protein. The results are shown in Table 3. As shown in Table 3, it became clear that the production amount of a Remicade-derived Fab-type antibody, with the Fd chain of which Asp was fused, was approximately 5 times higher than that of an unfused Remicade-derived Fab-type antibody, and that fusion of Asp was effective, regardless of the type of a Fab-type antibody.

TABLE 3

| fusion peptide | TOD600 | Fab (mg/L) |
| --- | --- | --- |
| none (control) | 55.3 | 0.006 |
| Asp | 56.7 | 0.032 |

(Comparative Example 9) Construction of Fab-Type Antibody Vector for *Pichia*

The pUC-LEU2-PmMfLTm-PmMfFtm described in Example 2 was treated with HindIII, and a vector fragment comprising a Fab-type antibody gene was then purified from agarose gel. Thereafter, the G418 resistance gene described in Example 15 was inserted into the HindIII site of this vector fragment to construct pUC-G418-PmMfLTm-PmMfFtm.

(Comparative Example 10) Obtainment of Transformant of *Pichia* Yeast

The wild-type *Pichia* yeast strain Y-11430 was transformed with the vector constructed in Comparative Example 9. The method described in Example 16 was applied herein.

(Comparative Example 11) Culture of Transformant and Preparation of Culture Supernatant A culture supernatant of the Fab-type antibody expression vector-introduced *Pichia* strain obtained in Comparative Example 10 was prepared in the same manner as the method described in Example 4.

(Comparative Example 12) Quantification of Fab-Type Antibody

The secretory production amount of a Fab-type antibody in the culture supernatant obtained in Comparative Example 11 was analyzed by a sandwich ELISA (Enzyme-Linked Immunosorbent Assay) method in the same manner as that of Example 5. The results are shown in Table 4.

(Example 15) Construction of Fab-Type Antibody Vector for *Pichia*

A G418 resistance gene (SEQ ID NO: 66) designed to express under the control of the GAP promoter of the *Ogataea polymorpha* yeast was totally synthesized, and it was then used as a template for PCR. A gene fragment having HindIII sites at both ends of this G418 resistance gene was prepared by PCR using primers 46 and 47 (SEQ ID NO: 67 and 68), and it was then treated with HindIII. The Fab-type antibody expression vectors each comprising an Fd chain gene containing a nucleotide sequence encoding Asp described in Example 2 were each treated with HindIII, and vector fragment comprising a Fab-type antibody gene was purified from agarose gel. Thereafter, the aforementioned G418 resistance gene was inserted into the HindIII site of this vector fragment, so as to construct each Fab-type antibody expression vector comprising an Fd chain gene containing a nucleotide sequence encoding Asp, in which the G418 resistance gene was used as a selection marker.

(Example 16) Obtainment of Transformant of *Pichia*

The wild-type *Pichia* yeast strain Y-11430 was transformed with each Fab-type antibody expression vector comprising an Fd chain gene containing a nucleotide sequence encoding Asp constructed in Example 15, in which the G418 resistance gene was used as a selection marker. Transformation was carried out by the same method as that described in Example 3, with the exception that *Pichia* yeast was used instead of *Hansenula* yeast.

After completion of the transformation, the cell mass was applied onto a G418-containing SD medium agar plate (0.17% bacto yeast nitrogen base w/o amino acids and ammonium sulfate (manufactured by Difco), 0.1% sodium glutamate, 1% glucose, and 0.25 g/L G418), and it was then subjected to a static culture at 30° C. for 3 days, so that a strain growing in the static culture was selected, thereby obtaining a Fab-type antibody-expressing strain.

(Example 17) Culture of Transformant and Preparation of Culture Supernatant

A culture supernatant of the *Pichia* yeast Fab-type antibody expression vector-introduced strain obtained in Example 16 was prepared in the same manner as the method described in Example 4.

(Example 18) Quantification of Fab-Type Antibody

The secretory production amount of a Fab-type antibody in the culture supernatant obtained in Example 17 was analyzed by a sandwich ELISA (Enzyme-Linked Immunosorbent Assay) method in the same manner as that of Example 5.

The Fab-type antibody in the culture supernatant was quantified using a calibration curve of standard protein. The results are shown in Table 4. As shown in Table 4, it became clear that the production amount of the Fab-type antibody, with the Fd strain of which Asp was fused, was approximately 2 times higher than that of an unfused Fab-type antibody, and that fusion of Asp was effective for a plurality of yeast species.

TABLE 4

| fusion peptide | TOD600 | Fab (mg/L) |
| --- | --- | --- |
| none (control) | 64.8 | 3.3 |
| Asp | 62.6 | 6.4 |

(Example 19) Construction 3 of Various Fab-Type Antibody Expression Vectors

A fragment, with which a nucleotide sequence encoding an Fd chain, a nucleotide sequence (SEQ ID NO: 70) encoding a peptide consisting of Asp-Lys-Thr-His-Thr-Asp-Lys-Thr-His-Thr (SEQ ID NO: 69), and a nucleotide sequence encoding a termination codon were fused, was prepared by PCR. An Fd chain gene fragment, with which a nucleotide sequence encoding Asp-Lys-Thr-His-Thr-Asp-Lys-Thr-His-Thr (SEQ ID NO: 69) was fused, was obtained by performing PCR using primer 15 and primer 48 (SEQ ID NO: 71), and also using, as a template, the Fab-type antibody expression vector comprising an Fd chain gene containing a nucleotide sequence encoding Asp-Lys-Thr-His-Thr (SEQ ID NO: 2), as prepared in Example 2. This fragment was treated with BglII, and was then inserted into the BglII site of the pUC-LEU2-PmMfTm described in Example 1, so as to construct a plasmid comprising an Fd chain gene containing a nucleotide sequence encoding Asp-Lys-Thr-His-Thr-Asp-Lys-Thr-His-Thr (SEQ ID NO: 69). Using pUC-LEU2-PmMfLTm as a template, a gene fragment having EcoRI sites at both ends of a gene fragment, to which a MOX promoter, MFα, an L chain, and some of a MOX terminator were ligated, was prepared by PCR using primers 13 and 14. This gene fragment was treated with EcoRI, and was then inserted into the EcoRI site of a plasmid comprising an Fd chain gene containing a nucleotide sequence encoding Asp-Lys-Thr-His-Thr-Asp-Lys-Thr-His-Thr (SEQ ID NO: 69), so as to construct a Fab-type antibody expression vector comprising an Fd chain gene containing a nucleotide sequence encoding Asp-Lys-Thr-His-Thr-Asp-Lys-Thr-His-Thr (SEQ ID NO: 69).

(Example 20) Obtainment of Transformant

The recombinant vector expressing a Fab-type antibody constructed in Example 19 was cleaved with the EcoRV site in the MOX terminator, so as to linearize it. This fragment was used to transform *Ogataea polymorpha* according to the method described in Example 2, so as to obtain a Fab-type antibody-expressing strain.

(Example 21) Culture of Transformant and Preparation of Culture Supernatant

A culture supernatant of the Fab-type antibody-expressing strain obtained in Example 20 was prepared in the same manner as that of Example 3.

(Example 22) Quantification of Fab-Type Antibody

The secretory production amount of a Fab-type antibody in the culture supernatant obtained in Example 21 was analyzed by the method described in Example 4.

The Fab-type antibody in the culture supernatant was quantified using a calibration curve of standard protein. The results are shown in Table 5. As shown in Table 5, the production amount of the Fab-type antibody, with the Fd chain of which a peptide consisting of 10 residues was fused, was approximately 5 times higher than that of an unfused Fab-type antibody.

TABLE 5

| fusion peptide | TOD600 | Fab (mg/L) |
| --- | --- | --- |
| none (control) | 40.5 | 0.55 |
| Asp-Lys-Thr-His-Thr-Asp-Lys-Thr-His-Thr (SEQ ID NO: 69) | 38.8 | 2.64 |

(Example 23) Construction 4 of Fab-Type Antibody Expression Vector

A fragment, with which a nucleotide sequence encoding an Fd chain, a nucleotide sequence (SEQ ID NO: 75) encoding a peptide consisting of 30 residues (SEQ ID NO: 74), and a nucleotide sequence encoding a termination codon were fused, was prepared by PCR.

An Fd chain gene fragment, with which a nucleotide sequence encoding the peptide of SEQ ID NO: 74 was used, was obtained by performing PCR using primer 49 (SEQ ID NO: 76) and primer 50 (SEQ ID NO: 77), and also using, as a template, pEGFP-F (manufactured by Clontech) or the like. This fragment was treated with BglII and BamHI, and was then inserted into the BglII site of the pUC-LEU2-PmMfTm described in Example 1, so as to obtain a plasmid comprising a portion of the nucleotide sequence encoding the peptide of SEQ ID NO: 74. Subsequently, PCR was carried out using primer 15 and primer 51 (SEQ ID NO: 78) to obtain an Fd chain gene fragment. This fragment was treated with BglII and BamHI, and was then inserted into the BglII site of the aforementioned plasmid comprising a portion of the nucleotide sequence encoding the peptide of SEQ ID NO: 74, so as to construct a vector comprising a Fd chain gene, with which the nucleotide sequence encoding the peptide of SEQ ID NO: 74 was used. Using pUC-LEU2-PmMfLTm as a template, a gene fragment having EcoRI sites at both ends of a gene fragment, to which a MOX promoter, MFα, an L chain, and some of a MOX terminator were ligated, was prepared by PCR using primers 13 and 14. This gene fragment was treated with EcoRI, and was then inserted into the EcoRI site of a vector comprising an Fd chain gene, with which the nucleotide sequence encoding the peptide of SEQ ID NO: 74 was fused, so as to construct a Fab-type antibody expression vector comprising the Fd chain gene containing the nucleotide sequence encoding the peptide of SEQ ID NO: 74.

(Example 24) Obtainment of Transformant

The recombinant vector expressing a Fab-type antibody constructed in Example 23 was cleaved with the EcoRV site in the MOX terminator, so as to linearize it. This fragment was used to transform *Ogataea polymorpha* according to the method described in Example 2, so as to obtain a Fab-type antibody-expressing strain.

(Example 25) Culture of Transformant and Preparation of Culture Supernatant

A culture supernatant of the Fab-type antibody-expressing strain obtained in Example 24 was prepared in the same manner as that of Example 3.

(Example 26) Quantification of Fab-Type Antibody

The secretory production amount of a Fab-type antibody in the culture supernatant obtained in Example 25 was analyzed by the method described in Example 4.

The Fab-type antibody in the culture supernatant was quantified using a calibration curve of standard protein. The results are shown in Table 6. As shown in Table 6, it became clear that the production amount of the Fab-type antibody, with the Fd chain of which a peptide consisting of 30 residues was fused, was approximately 4 times higher than that of an unfused Fab-type antibody.

TABLE 6

| fusion peptide | TOD600 | Fab (mg/L) |
| --- | --- | --- |
| none (control) | 40.5 | 0.55 |
| Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO: 74) | 40.4 | 2.09 |

The invention claimed is:

1. A method for producing a Fab-type antibody, which comprises a step of culturing a transformant and then recovering a Fab-type antibody,
wherein the transformant is obtained by transforming a host with a recombinant vector,
wherein the host is yeast,
wherein the recombinant vector comprises a nucleotide sequence encoding an amino acid or an amino acid sequence capable of increasing a secretion amount of Fab-type antibody at 3'-terminus of a nucleotide sequence encoding an amino acid sequence of Fd chain or L chain of an antibody;
wherein the amino acid or the amino acid sequence capable of increasing the secretion amount of a Fab-type antibody is any one of Asp, Gly, Ala, Val, Leu, Ile, Cys, Met, Ser, Thr, Tyr, Phe, Trp, Pro, Glu, Asn, Gln, Lys, Arg, His, Asp-Lys, Asp-Lys-Thr, Asp-Lys-Thr-His (SEQ ID NO:1), Asp-Lys-Thr-His-Thr-Asp-Lys-Thr-His-Thr (SEQ ID NO:69), and Gly-Gly-Gly-Gly-Ser-Met-Val-Ser-Lys-Gly-Glu-Glu-Leu-Phe-Thr-Gly-Val-Val-Pro-Ile-Leu-Val-Glu-Leu-Asp-Gly-Asp-Val-Asn-Gly (SEQ ID NO:74), or a combination thereof,
provided that a histidine tag consisting of a multiple number of His is excluded, and
provided that an amino acid sequence capable of increasing the secreation amount of a Fab-type antibody of Asp-Lys-Thr-His-Thr (SEQ ID NO: 2) is excluded, and
wherein the recombinant vector has any of the following alignment of individual constituents from the 5'-terminal side to the 3'-terminal side:
(1) first promoter sequence-first signal sequence-L chain gene-second promoter sequence-second signal sequence-Fd chain gene-terminator sequence;
(2) first promoter sequence-first signal sequence-Fd chain gene-second promoter sequence-second signal sequence-L chain gene-terminator sequence; and
(3) a combination of an expression vector comprising (first promoter sequence-first signal sequence-L chain gene-first terminator sequence), with an expression vector comprising (second promoter sequence-second signal sequence-Fd chain gene-second terminator sequence).

2. The method according to claim 1, wherein the recombinant vector is any one of the following (a) to (c):
   (a) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene of an antibody;
   (b) a recombinant vector, which comprises an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody, and a Fd chain gene of an antibody; and
   (c) a recombinant vector, which comprises an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody.

3. The method according to claim 1, wherein the host is transformed with a combination of recombinant vectors, wherein the combination of recombinant vectors is any one of the following (A) to (C):
   (A) a combination of a recombinant vector comprising an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and a recombinant vector comprising the L chain gene of an antibody;
   (B) a combination of a recombinant vector comprising an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody, and a recombinant vector comprising the Fd chain gene of an antibody; and
   (C) a combination of a recombinant vector comprising an Fd chain gene comprising a nucleotide sequence encoding an amino acid or an amino acid sequence capable of increasing the secretion amount of a Fab-type antibody at the 3'-terminus of a nucleotide sequence encoding the amino acid sequence of the Fd chain of an antibody, and a recombinant vector comprising an L chain gene comprising a nucleotide sequence encoding an amino acid or an amino acid sequence capable of increasing the secretion amount of a Fab-type antibody at the 3'-terminus of a nucleotide sequence encoding the amino acid sequence of the L chain of an antibody.

4. The method according to claim 1, wherein the yeast is yeast of the genus *Ogataea* or the genus *Komagataella*.

5. The method according to claim 4, wherein the yeast of the genus *Ogataea* or the genus *Komagataella* is *Ogataea polymorpha* or *Komagataella pastoris*.

6. The method according to claim 1, wherein when the transformant is cultured to produce a Fab-type antibody, the secretory production amount of a Fab-type antibody in a culture supernatant is 2.0 mg/L or more.

7. The method according to claim 1, wherein the amino acid or the amino acid sequence capable of increasing the secretion amount of the Fab-type antibody consist of 1 to 30 amino acids.

\* \* \* \* \*